US00RE51019E

(19) United States
(12) Reissued Patent
Burnett et al.

(10) Patent Number: US RE51,019 E
(45) Date of Reissued Patent: Sep. 1, 2026

(54) TOPICAL BRACHYTHERAPY DEVICE AND METHOD OF TREATMENT OF MALIGNANT CANCER

(71) Applicant: Margin-Clear Pty Ltd, Melbourne (AU)

(72) Inventors: David Burnett, Melbourne (AU); Daniel Croagh, Melbourne (AU); Mehrdad Nikfarjam, Melbourne (AU)

(73) Assignee: Margin-Clear Pty Ltd, Melbourne (AU)

(21) Appl. No.: 18/371,346

(22) Filed: Sep. 21, 2023

Related U.S. Patent Documents

Reissue of:
(64) Patent No.: 11,123,445
Issued: Sep. 21, 2021
Appl. No.: 16/979,125
PCT Filed: Mar. 7, 2019
PCT No.: PCT/AU2019/050201
§ 371 (c)(1),
(2) Date: Sep. 8, 2020
PCT Pub. No.: WO2019/169445
PCT Pub. Date: Sep. 12, 2019

(30) Foreign Application Priority Data

Mar. 7, 2018 (AU) ..... 2018900745

(51) Int. Cl.
*A61K 51/12* (2006.01)
*A61N 5/10* (2006.01)

(52) U.S. Cl.
CPC ..... *A61K 51/1279* (2013.01); *A61N 5/1015* (2013.01); *A61N 5/1029* (2013.01); *A61N 2005/1094* (2013.01)

(58) Field of Classification Search
CPC .... A61K 51/1279; A61N 5/00; A61N 5/1015; A61N 5/1029; A61N 2005/1021; A61N 2005/1094; A61P 35/00
See application file for complete search history.

(56) References Cited

U.S. PATENT DOCUMENTS 3,351,049 A 11/1967 Lawrence
5,871,708 A * 2/1999 Park ..... A61K 51/1279 424/1.11

(Continued)

FOREIGN PATENT DOCUMENTS

CA 2171124 C 1/2001
EP 1008995 A1 6/2000

(Continued)

OTHER PUBLICATIONS

Supplementary European Search Report for Application No. EP 19 76 4767 dated Oct. 29, 2021, 1 page.

(Continued)

*Primary Examiner* — Elizabeth L Mckane
(74) *Attorney, Agent, or Firm* — Seed Intellectual Property Law Group LLP

(57) ABSTRACT

A flexible brachytherapy device includes a bioresorbable carrier matrix structure comprising a plurality of radio-isotope particles and having opposite first and second surfaces. The bioresorbable carrier matrix structure degrades, when implanted at a wound site, at a rate such that the bioresorbable carrier matrix structure has a half-life that is longer than a half-life of the plurality of radio-isotope particles. A hydrophilic substrate located adjacent to the first surface of the bioresorbable carrier matrix structure degrades, when implanted at the wound site, at a rate faster than the bioresorbable carrier matrix structure. A hydrogel substrate located adjacent to the second surface of the bioresorbable carrier matrix structure shields radioactivity and degrades at a rate such that the hydrogel substrate has a half-life that is longer than the half-life of the plurality of radio-isotope particles.

34 Claims, 14 Drawing Sheets

(56) References Cited

U.S. PATENT DOCUMENTS

| | | | | |
|---|---|---|---|---|
| 6,149,889 | A * | 11/2000 | Chin | A61K 51/02 264/641 |
| 6,248,057 | B1 | 6/2001 | Mavity et al. | |
| 6,575,887 | B1 | 6/2003 | Schrayer | |
| 6,749,554 | B1 | 6/2004 | Snow et al. | |
| 9,486,642 | B2 * | 11/2016 | Cipriani | A61N 5/1029 |
| 2001/0044567 | A1 | 11/2001 | Zamora et al. | |
| 2001/0051766 | A1 | 12/2001 | Gazdzinski | |
| 2002/0055667 | A1 | 5/2002 | Mavity et al. | |
| 2003/0204125 | A1 * | 10/2003 | Brauckman | A61N 5/1027 600/3 |
| 2003/0233136 | A1 * | 12/2003 | Williams | A61N 5/1027 607/50 |
| 2006/0116696 | A1 * | 6/2006 | Odermatt | A61L 31/16 623/23.72 |
| 2006/0269475 | A1 | 11/2006 | Ryu et al. | |
| 2007/0016179 | A1 * | 1/2007 | Francescatti | A61B 90/04 606/33 |
| 2015/0104380 | A1 | 4/2015 | Chang et al. | |
| 2015/0306420 | A1 | 10/2015 | Strauss et al. | |
| 2020/0188691 | A1 | 6/2020 | Sarazin et al. | |
| 2020/0276007 | A1 * | 9/2020 | Musara | A61L 31/005 |
| 2020/0397929 | A1 | 12/2020 | Burnett et al. | |

FOREIGN PATENT DOCUMENTS

| | | | | |
|---|---|---|---|---|
| EP | 1 536 746 | B1 | 5/2013 | |
| WO | 97/19706 | A | 6/1997 | |
| WO | WO-9719706 | A1 * | 6/1997 | A61N 5/1027 |
| WO | 02/100480 | A2 | 12/2002 | |
| WO | 2007/052267 | A2 | 5/2007 | |
| WO | 2007/106531 | A1 | 9/2007 | |
| WO | 2008/024959 | A2 | 2/2008 | |
| WO | 2009/029224 | A1 | 3/2009 | |
| WO | 2009/134431 | A1 | 11/2009 | |
| WO | 2011/084465 | A2 | 7/2011 | |
| WO | 2017/173352 | A1 | 10/2017 | |
| WO | 2018/009839 | A1 | 1/2018 | |
| WO | 2019169445 | A1 | 9/2019 | |
| WO | 2022201130 | A1 | 9/2022 | |

OTHER PUBLICATIONS

Qu et al., "Encapsulation of isotope on novel ß-emitting poly(ethyleneterephthalate) surfaces", Journal of Biomedical Materials Research, 2001, vol. 57, pp. 619-623.

Karsh et al., "Absorbable Hydrogel Spacer Use in Prostate Radiotherapy: A Comprehensive Review of Phase 3 Clinical Trial Published Data", Urology, 2017, vol. 115, pp. 39-44.

International Search Report and Written Opinion, dated Dec. 10, 2024, for International Patent Application No. PCT/AU2024/051008. (11 pages).

International Search Report for Application No. PCT/AU2019/050201 dated Mar. 26, 2019, 8 pgs.

International Preliminary Report on Patentability (Chapter II of the Patent Cooperation Treaty) for Application No. PCT/AU2019/050201 dated Jun. 16, 2020, 41 pgs.

Article 15 International-type search for AU provisional patent application No. 2018900745 dated Dec. 18, 2018, 16 pgs.

Kaplan et al., "A comparison of the precision of seeds deposited as loose seeds versus suture embedded seeds: a randomized trial", Brachytherapy, 2004, vol. 3, No. 1, pp. 7-9.

Häfeli et al., "Fibrin glue system for adjuvant brachytherapy of brain tumors with $^{188}$Re and $^{186}$Re-labeled microspheres", European Journal of Pharmaceutics and Biopharmaceutics, 2007, vol. 65, No. 3, pp. 282-288.

Salgueiro et al., "Bioevaluation of $^{32}$P patch designed for the treatment of skin diseases", ScienceDirect, www.sciencedirect.com, Nuclear Medicine and Biology 35, 2008, pp. 233-237.

Rahman et al., "Adjuvant Chemotherapy for Brain Tumors Delivered via a Novel Intra-Cavity Moldable Polymer Matrix," PLOS ONE, www.plosone.org, Oct. 2013, vol. 8, Issue 10, e77435, 12 pgs.

Lee et al., "Surface coating for prevention of metallic seed migration in tissues", Medial Physics, 2015, vol. 42, No. 6, pp. 2805-2812.

* cited by examiner

TOPICAL BRACHYTHERAPY DEVICE AND METHOD OF TREATMENT OF MALIGNANT CANCER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application claims priority from Australian Provisional Patent Application No 2018900745, filed 7 Mar. 2018, the contents of which are incorporated herein by reference in their entirety.

BACKGROUND

Technical Field

The present disclosure relates to a brachytherapy device for application on a wound site in a body. The device may, in some examples, be used to treat cancers of the body.

Description of the Related Art

Cancer is a disease of the cells that impacts multiple body organs and affects a large number of people throughout the world. When normal mechanisms for regulating the growth of cells in the body are disturbed, cells can begin to grow in an uncontrolled fashion. A cancer develops when normal cells in the body begin to develop an abnormal growth pattern, and do not undergo the normal cell lifecycle including cell death. The uncontrolled rapid growth, and invasion of normal tissue by abnormal cells is the definition of malignant cancer. Cancer cells may undergo metastasis whereby they detach from their primary site and travel to other parts of the body where they begin to grow new tumor deposits.

Treatments for cancer can include surgery, chemotherapy, and radiation therapy or combinations thereof. Surgery is usually the treatment of choice for most cancers if the cancer appears localized to an organ, and initial work up of a patient to determine whether the tumor is removable by surgical means. Some cancers are amenable to surgical resection of metastatic deposits, such as colorectal, melanoma, and neuroendocrine tumors.

In surgical removal of a cancerous tumor, it is important to completely remove or destroy all the malignant cells. Surgical removal of cancer involves cutting out the tumor or tumors, including a margin of normal tissue around the cancer to ensure the entire disease is excised. This often includes removal of the lymph nodes to which the primary tumor may spread. Generally, a pathological examination of the resection margin of the tissue that is removed is employed at the time of surgery to ensure that the tumor has been completely removed.

One of the most feared complications of major cancer surgery is incomplete resection, or the presence of microscopic tumor cells at the resection margin. The likelihood of such an occurrence is reduced but not eliminated by the use of frozen section histology, which has a greatly reduced accuracy without the facility of immunohistochemistry to identify tumor cells. Secondly, many cancers infiltrate along lymphatic channels or follow perineal lymphatics where they are impossible to detect at the time of surgery.

Tumor cells can be left behind during cancer surgery because they have invaded into a critical structure that cannot be safely resected or reconstructed in an individual patient. In many cases, the index operation is such a physical and metabolic insult to the patient's physiology that re-operation and further resection is just not possible. In these cases, survival of the individual patient with positive margins is greatly and significantly reduced from an equivalent patient with clear margins.

The current process to manage close or positive margins is chemotherapy with or without adjuvant radiotherapy to the operative bed. This treatment is often ineffective at preventing local recurrence, and highly toxic. The doses of radiation achieved by the tumor cells are severely limited because of the presence of radiosensitive surrounding structures like the bowel, and the need to wait for reconstructed structures (like anastomoses) to heal before the commencement of chemotherapy.

This results in an ineffective radiation dose to the operative bed for tumor control, and a delay often up to 8-10 weeks before chemotherapy is instituted. In this time, the immunological/inflammatory insult of major surgery decreases the body's ability to fight tumor cells, and the cells at positive margin are left untreated, which results often in local recurrence, which can then metastasize throughout the body.

Recently the utility for high dose rate brachytherapy devices for managing inoperable tumors has increasingly been recognized. Radio-isotopes devised from beta emitting particles injected intra-arterially have shown potential in managing inoperable liver tumors, and beta-emitters suspended in a silica diluent has shown early potential for injection or positioning directly into inoperable pancreatic tumors through special applicators inserted into body cavities or tissues. There is however currently no suitable device for the routine management of the risk to the patient of positive margins post-surgery, and current devices based on the prior art are not useful as a routine surgical adjunct. Barriers to creation of such a routine surgical device include high cost, moderate inflexibility, non-bioresorbable radio-isotope sources, and a lack of absorbable unidirectionality.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

BRIEF SUMMARY

Brachytherapy devices of the prior art are often inflexible and not fully bioabsorbable and bioresorbable by the body. This is because of the use of non-bioabsorbable/bioresorbable radio-isotope sources, or metallic shields used to make the device unidirectional. This in turn does not allow accurate imaging of the site after resection. Inflexible brachytherapy devices of the prior art are also not suitable for an adjunctive approach to surgery as they are not able to fully conform to the operative bed, providing a uniform dose to every cell. Devices of the prior art have facilitated the production of discrete metallic sealed sources, which may be connected together by a flexible membrane. They are limited in conformability, in dose distribution, and by being non-absorbable in the body. Foreign objects, like brachytherapy seeds of the prior art, which are permanently implanted in the body (particularly in a surgical field which is potentially contaminated with microorganisms) have a very high risk of chronic infection and severe morbidity for the patient. This risk is not mitigated with a partially absorbable device, if there is any long term residual material in the brachytherapy seeds. It is therefore desirable for a brachytherapy device to be flexible, unidirectional (so that the surgeon and operating theatre staff have minimal exposure to radiation) and fully bioresorbable in the body, such that no foreign or metallic material remains in the long term.

Disclosed herein, in various embodiments, is a flexible brachytherapy device for application on a wound site in a body, the device comprising: a bioresorbable carrier matrix structure comprising a plurality of radio-isotope particles, the bioresorbable carrier matrix structure configured to degrade, when implanted at the wound site, at a rate substantially longer than a half-life of the plurality of radio-isotope particles such that activity from the plurality of radio-isotope particles is localized to the wound site, wherein the bioresorbable carrier matrix structure has opposite first surface and second surfaces; a hydrophilic substrate located adjacent to the first surface of the bioresorbable carrier matrix structure, wherein the hydrophilic substrate adheres to the wound site, the hydrophilic substrate configured to degrade, when implanted at the wound site, at a rate shorter than the bioresorbable carrier matrix structure to prevent migration of the device during the half-life of the plurality of radio-isotope particles; and a hydrogel substrate located adjacent to the second surface of the bioresorbable carrier matrix structure, the hydrogel substrate configured to shield radioactivity and to degrade at a rate longer than the half-life of the plurality of radio-isotope particles.

The bioresorbable carrier matrix may be formed by adsorbing or dispersing an aqueous solution of a radio-isotope to a hydrophobic substance. The bioresorbable carrier matrix may be further formed by precipitating the radio-isotope to form a plurality of insoluble radio-isotope particles in the bioresorbable carrier matrix structure.

The hydrophobic substance may comprise a hydrophilic surface to form the bioresorbable carrier matrix structure. The aqueous solution may comprise radioactive ions.

The radioactive ions are derived from one or more of: monosodium phosphate, disodium phosphate, potassium phosphate, dipotassium phosphate, orthophosphoric acid or tetrasodium pyrophosphate or soluble compounds containing iodide.

The bioresorbable carrier matrix structure may be configured with material(s) degradable by enzymatic processes. The bioresorbable carrier matrix structure may be configured with material(s) degradable by pyrophosphatase.

The bioresorbable carrier matrix structure may be provided by adsorbing or dispersing an aqueous solution of a radio-isotope to an amorphous or semicrystalline hydrophobic substance to provide the bioresorbable carrier matrix structure. The amorphous or semicrystalline hydrophobic substance may comprise a hydrophilic surface.

The plurality of radio-isotope particles may comprise elements in the compound molecules of calcium phosphate. The compound molecules of calcium phosphate may comprise one or more of: calcium pyrophosphate, monocalcium phosphate, dicalcium phosphate, octacalcium phosphate, tricalcium phosphate, hydroxyapatite, fluoroapatite or tetracalcium phosphate.

The precipitant may comprise an aqueous solution of calcium ions. The precipitant may comprise one or more of calcium chloride, calcium hydroxide, calcium nitrate or calcium bromide.

The bioresorbable carrier matrix may be amorphous or semicrystalline in nature. The bioresorbable carrier matrix may be partially semicrystalline, such that the rate of degradation of the device is based on the half-life of the plurality of radio-isotope particles and through modification of crystallinity.

In the device, the hydrogel substrate may be crosslinked with citric acid, wherein a percentage of citric acid is selected to specify the rate that the hydrogel substrate degrades to maintain structural integrity and shielding capacity. The percentage may be between 2.5% and 10%. The citric acid crosslinking may be catalyzed by titanium oxide.

The device may further comprise an inert adhesive layer located adjacent to a surface of the hydrogel substrate, wherein the inert adhesive layer is configured to adhere to the wound site.

The device may further comprise a removable film located adjacent to the inert adhesive layer, wherein the removable film is removable from the inert adhesive layer to expose a surface of the inert adhesive layer to the wound site.

Also disclosed herein, in various embodiments, is a method of manufacturing a flexible brachytherapy device for application on a wound site in a body, the method comprising: forming a bioresorbable carrier matrix structure comprising a plurality of radio-isotope particles, wherein the bioresorbable carrier matrix structure is configured to degrade at a rate substantially longer than a half-life of the radio-isotope particles such that activity from the plurality of radio-isotope particles is localized to the wound site, wherein the biodegradable carrier matrix structure has opposite first surface and second surfaces; forming a hydrophilic substrate adjacent to the first surface of the bioresorbable carrier matrix structure, wherein the hydrophilic substrate adheres to the wound site, the hydrophilic substrate configured to degrade, when implanted at the wound site, at a rate shorter than the bioresorbable carrier matrix structure to prevent migration of the device during the half-life of the plurality of radio-isotope particles; and forming a hydrogel substrate adjacent to the second surface of the bioresorbable carrier matrix structure, the hydrogel substrate configured to shield radioactivity and to degrade at a rate longer than the half-life of the plurality of radio-isotope particles.

In the method, the bioresorbable carrier matrix structure may be formed by: adsorbing or dispersing an aqueous solution of a radio-isotope to a hydrophobic substance. The bioresorbable carrier matrix structure may be formed by precipitating the radio-isotope to form a plurality of insoluble radio-isotope particles in the bioresorbable carrier matrix structure. The hydrophobic substance may comprise a hydrophilic surface.

The aqueous solution may comprise radioactive ions.

In the method, the bioresorbable carrier matrix structure may be formed by: adsorbing or dispersing an aqueous solution of a radio-isotope to an amorphous or semicrystalline hydrophobic substance to provide the resorbable carrier matrix structure. The amorphous or semicrystalline hydrophobic substance may comprise a hydrophilic surface.

A bioresorbable carrier matrix structure comprising a plurality of radio-isotope particles, wherein the bioresorbable carrier matrix structure is formed by: adsorbing or dispersing an aqueous solution of a radio-isotope to a hydrophobic substance to produce the bioresorbable carrier matrix structure. The bioresorbable carrier matrix structure may be formed by precipitating the radio-isotope to form a plurality of insoluble radio-isotope particles in the bioresorbable carrier matrix structure. The hydrophobic substance may comprise a hydrophilic surface.

The aqueous solution may comprise radioactive ions.

The bioresorbable carrier matrix structure may be formed by: adsorbing or dispersing a plurality of insoluble radio-isotope particles to an amorphous or semicrystalline hydrophobic substance to provide the bioresorbable carrier matrix structure. The amorphous or semicrystalline hydrophobic substance may comprise a hydrophilic surface.

The bioresorbable carrier matrix structure may be amorphous or semicrystalline in nature.

The bioresorbable carrier matrix structure may be configured to degrade, when implanted at a wound site, at a rate substantially longer than a half-life of the plurality of radio-isotope particles such that activity from the plurality of insoluble radio-isotope particles is localized to the wound site.

The bioresorbable carrier matrix may be configured to be used in a brachytherapy device for application on a wound site, the device comprising: a hydrophilic substrate located adjacent to a first surface of the bioresorbable carrier matrix structure, wherein the hydrophilic substrate adheres to the wound site, the hydrophilic substrate configured to degrade, when implanted at the wound site, at a rate shorter than the bioresorbable carrier matrix structure to prevent migration of the device during the half-life of the plurality of radio-isotope particles.

The bioresorbable carrier matrix may be configured to be used in a brachytherapy device for application on a wound site, the device comprising: a hydrogel substrate located adjacent to a second surface of the bioresorbable carrier matrix structure, the hydrogel substrate configured to shield radioactivity and degrade at a rate longer than the half-life of the plurality of radio-isotope particles.

Further disclosed herein is a method for manufacturing a bioresorbable carrier matrix comprising a plurality of radio-isotope particles, the method comprising: adsorbing or dispersing an aqueous solution of a radio-isotope to a hydrophobic substance. The bioresorbable carrier matrix may be formed by precipitating the radio-isotope to form a plurality of insoluble radio-isotope particles in the bioresorbable carrier matrix structure. The hydrophobic substance may comprise a hydrophilic surface.

The aqueous solution may comprise radioactive ions.

Also disclosed herein is an applicator device for application of a brachytherapy device to a wound site in a body, the applicator device comprising: an upper housing having a recess to receive a brachytherapy device; a removable base attached with the upper housing, wherein when attached the removable base and upper housing shield radiation from the brachytherapy device; wherein the removable base is removable from the upper housing to expose a first surface of the brachytherapy device to a wound site.

The removable base may be slidably attached with the upper housing and slidably removable from the upper housing.

The upper housing may further comprise an inlet port fluidly connected to the recess, to allow introduction of a fluid through the inlet port to the brachytherapy device in the recess.

The applicator device may further comprise a soluble adhesive to additionally secure the upper housing and the removable base, wherein the soluble adhesive is dissolvable by a liquid introduced into the recess to allow the removable base to be slidably removed from the upper housing.

The upper housing may comprise a transparent, semi-transparent, or translucent material to shield beta radiation. The upper housing may be formed of an acrylate polymer.

The applicator device may further comprise a handle at the upper housing to assist placement of the applicator device and brachytherapy device to a wound site.

Further disclosed is a brachytherapy system comprising: the applicator device as described above, and the brachytherapy device as described above, wherein the hydrogel substrate is hydrated at equilibrium water content by the inlet port of the applicator device.

BRIEF DESCRIPTION OF THE SEVERAL VIEWS OF THE DRAWINGS

Examples of the present disclosure will be described with reference to the figures below.

DETAILED DESCRIPTION

Overview

Figure 1:
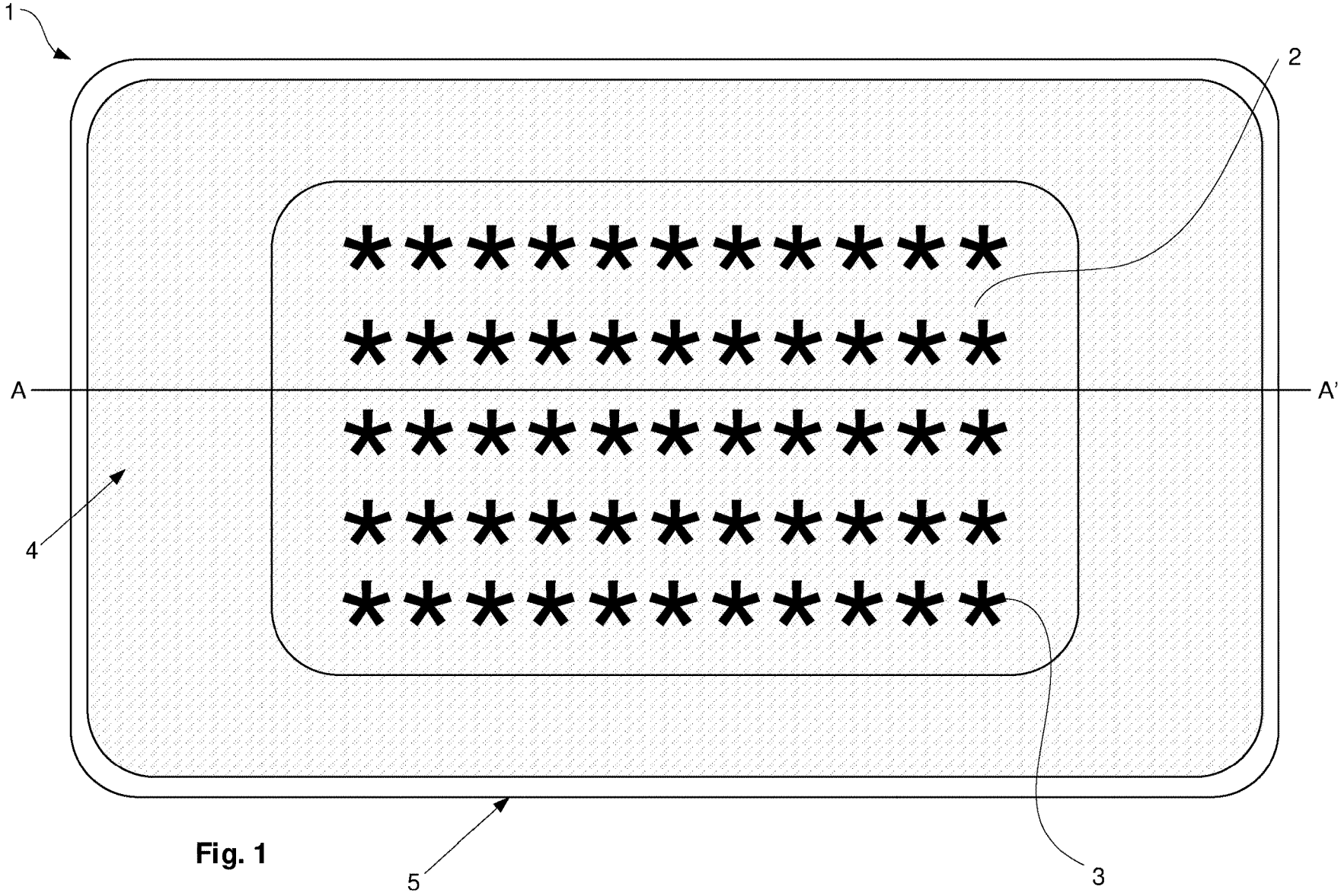
FIG. 1 illustrates a schematic representation of a brachytherapy device.

An example of a brachytherapy device is illustrated in FIG. 1. The device 1 may be used on a wound site in a body, for example during surgery. The device 1 comprises a bioresorbable carrier matrix structure 2 comprising a plurality of radio-isotope particles 3. The bioresorbable carrier matrix structure 2 is configured to degrade, when implanted at the wound site, at a rate substantially longer than a half-life of the plurality of radio-isotope particles 2. In this way, activity from the plurality of radio-isotope particles 2 is localized to the wound site. The bioresorbable carrier matrix structure 2 has opposite first surface and second surfaces 21, 22.

The device 1 further comprises a hydrophilic substrate 4 located adjacent to the first surface 21 of the bioresorbable carrier matrix structure 2. The hydrophilic substrate 4 adheres to the wound site. The hydrophilic substrate is configured to degrade, when implanted at the wound site, at a rate shorter than the bioresorbable carrier matrix structure to prevent migration of the device during the half-life of the plurality of radio-isotope particles 3.

The device 1 further comprises a hydrogel substrate 5 located adjacent to the second surface 22 of the bioresorbable carrier matrix structure 2. In some examples, the hydrogel substrate 5 is adherent to and integrated with the hydrophilic substrate 4. The hydrogel substrate 5 is configured to shield radioactivity and to degrade at a rate longer than the substantial activity of the plurality of radio-isotope particles 3, for example at a rate longer than the half-life of the plurality of radio-isotope particles 3. In this way, the hydrogel substrate 5 shields radioactivity until radioactive decays renders the bioresorbable carrier matrix structure 2 to be substantially inactive (of radioactivity) and safe.

The device 1 may be suitable for minimizing and/or controlling local recurrence of malignant cancer and seroma following cancer surgery. The device 1 may also be suitable for minimizing and/or controlling uncontrolled growth of microscopic tumor cells at the resected margin of surgery.

It is an advantage that the device 1 is configured to be completely bioabsorbable and/or bioresorbable in the body. In this way, the device may be completely degraded/replaced "in vivo." Furthermore, the device 1 also has the advantage of being a fully sealed source (while significantly radioactive). In some examples, the device 1 is constructed such that it can withstand immersion in water. phosphate buffered saline or other physiological compatible fluid at room temperature for 24 hours without significant loss of radio-isotope.

It is a further advantage that the plurality of radio-isotope particles 3 are maintained in place in the wound site until the time they are no longer substantially radioactive.

It is yet a further advantage that the brachytherapy device 1 is configured to be flexible and conform to the wound site.

Details of an exemplary brachytherapy device 1 will now be described in detail.

Bioresorbable Carrier Matrix 2

As described above, the device 1 comprises a bioresorbable carrier matrix structure 2 comprising a plurality of radio-isotope particles 3. In some examples, the bioresorbable carrier matrix 2 is formed by adsorbing or dispersing an aqueous solution of a radio-isotope to a hydrophobic substance. The bioresorbable carrier matrix may further be formed by precipitating the radio-isotope to form a plurality of insoluble radio-isotope particles in the bioresorbable carrier matrix structure 2. In this example, the aqueous solution may comprise radioactive ions. The radioactive ions may comprise one or more of: monosodium phosphate, disodium phosphate, potassium phosphate, dipotassium phosphate, orthophosphoric acid or tetrasodium pyrophosphate or soluble compounds containing iodide.

The plurality of radio-isotope particles 3 may comprise a beta-emitter. In other examples, the plurality of radio-particles 3 may comprise a gamma emitter or a mixed gamma/beta emitter. In some examples, the plurality of radio-isotope particles 3 may be elements in the family of calcium phosphate compounds. In one example, the plurality of radio-isotope particles 3 may comprise elements in the compound molecule of calcium pyrophosphate. This may comprise the compound molecules of: calcium phosphate, monocalcium phosphate, dicalcium phosphate, octacalcium phosphate, tricalcium phosphate, hydroxyapatite, fluoroapatite or tetracalcium phosphate. In some examples, the plurality of radio-isotope particles 3 may comprise the compound molecules in a hydrated or anhydrous form.

In other examples, the plurality of radio-isotope particles 3 may comprise one or more of: Yttrium-90, Iridium-192, Palladium-103, Caesium-[137] *131*, Iodine-131, Iodine-125, Iodine-123, 33-phosphorus (33P), 32-phosphorus (32P) or a ratio of 33-phosphorus to 32-phosphorus and/or compounds containing such isotopes. In some examples, the use of a ratio of 33P to 32P radio-isotope as the plurality of radio-isotope particles 3 reduces the collateral radiation exposure from handling compared to P32 alone. It is to be appreciated that in this description, radio-isotope particles 3 can include compounds that contain radio-isotopes.

The bioresorbable carrier matrix structure 2 is configured to degrade, when implanted at the wound site, at a rate substantially longer than a half-life of the plurality of radio-isotope particles 3. In this way, activity from the plurality of radio-isotope particles is localized to the wound site.

Figure 5:
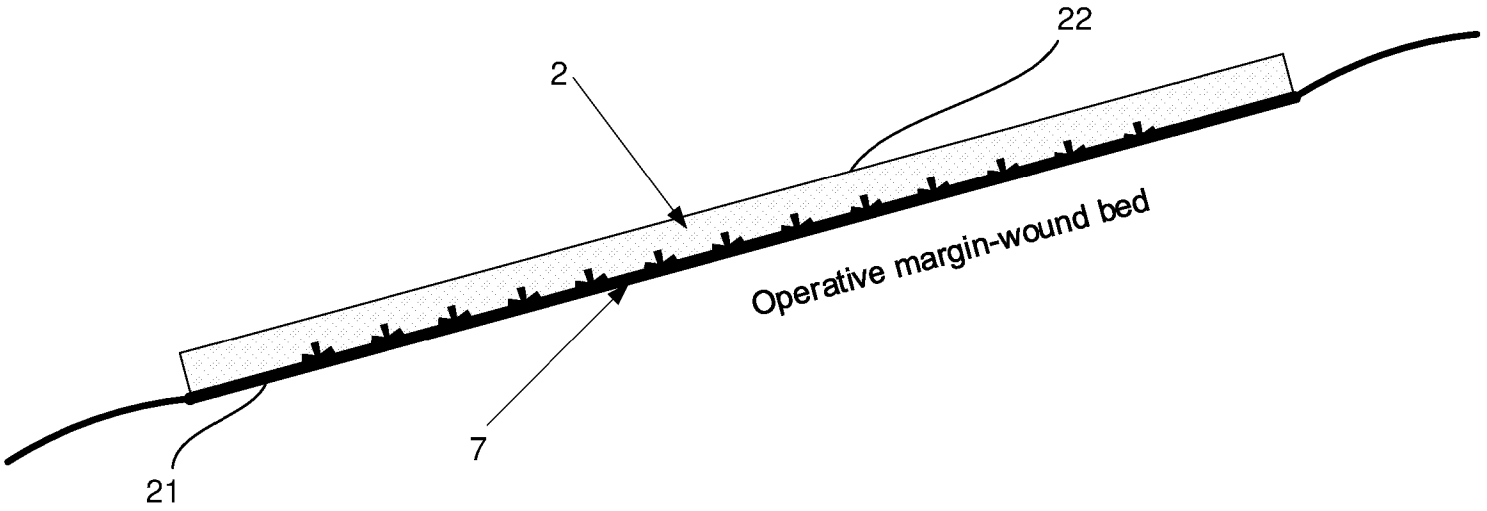
FIG. 5 illustrates a further cross-sectional schematic representation of a brachytherapy device, following further absorption of the hydrophilic substrate, degradation of the hydrogel and decay of the radio-isotope.

FIG. 5 illustrates a cross-sectional view of the device 1 after significant nuclear decay of the plurality of radio-isotope particles 3. As shown, after degradation of the hydrophilic substrate 4, hydrogel 5 and nuclear decay of the plurality of radio-isotope particles 3, the bioresorbable carrier matrix structure 2 remains in place. Having the bioresorbable carrier matrix that persists longer than the substantial radioactivity of the radio-isotope (such as over a half-life of the radio-isotope) ensures that radioactivity is localized to the wound site 100 at the operative margin-wound bed 7.

The rate of delivery of the radiation from the plurality of radio-isotope particles 3 may be determined by characteristics of the bioresorbable carrier matrix structure 2 and/or the hydrophilic substrate 4.

In some examples, the plurality of radio-isotope particles 3 may comprise medium (under 30 days) half-life particles. In this way, the bioresorbable carrier matrix structure 2 may degrade at a rate substantially longer than 30 days.

The bioresorbable carrier matrix structure 2 may be formed by adsorbing or dispersing a plurality of insoluble radio-isotope particles to a hydrophobic substance with a hydrophilic surface. The hydrophobic substance may be microporous or macroporous.

In some examples, the hydrophobic substance may comprise a hydrophilic surface. In this way, as described below, a solution containing radioactive ions may be drawn up into a microporous hydrophobic substance by capillary action. Without the hydrophilic surface, the radioactive ions may not be distributed in that way. Alternatively, in an example of the hydrophobic substance without a hydrophilic surface, the radioactive particles may be hot pressed/imprinted onto the hydrophobic substance.

In one example, a microporous, hydrophobic substance with a hydrophilic surface is prepared as follows. A hydrophobic, biodegradable polymer such as polycaprolactone (PCL) is made hydrophilic with addition of a surfactant. In one example, the surfactant may comprise a polyethylene glycol-polypropylene glycol block monomer (Pluronic P123). In other examples, other hydrophobic base biopolymers may be used such as polylactide or racemers of polylactide such as poly-L Lactide, poly D-lactide, or Poly-DL lactide (PDLLA), or composites thereof.

In further examples, a hydrophilic copolymer may be added to improve hydrophilicity and available sites for crosslinking. Examples of a hydrophilic copolymer may comprise collagen, alginate, carboxymethylcellulose and other forms of cellulose, polyethylene glycol, or any of a large series of copolymers of polyethylene glycol. In some examples, a partially amorphous polymer such as PDLLA, or a biodegradable elastomer including but not limited to (poly)glycerol sebacate (or polyurethane based biodegradable elastomers) may be added to increase the flexibility of the PCL, reduce the percentage of crystallinity, and/or increase the hydrophilicity of the resultant blend.

The new slowly hydrolysable polymer blend is then made microporous through the incorporation of a very soluble substance, such as a soluble salt (NaCl, MgCl etc.) or soluble liquid (like glycerol) or other soluble component in a non-toxic solvent. The soluble component may be leached out of the PCL blend by a combination of heat and/or a solvent. This results in a microporous, hydrophobic matrix with a hydrophilic surface. The matrix may be slowly absorbing.

In some examples, the porosity of the hydrophobic substance/matrix may also be generated by bubbling of an inert gas during the mixing of polymers, such as in the extruder. The inert gas may comprise nitrogen, carbon dioxide or argon. In other examples, the porosity of the hydrophobic substance/matrix may be generated with the inclusion of 'porogen' compounds, such as sodium bicarbonate, in the formulation. In this way, gas may be released on exposure to heat.

In another example, a rapidly decaying radio-isotope may be used for the plurality of radio-isotope particles. This may facilitate the use of a purely hydrophilic carrier matrix as the bioresorbable carrier matrix structure 2, including polymers of polyglycolide or a crosslinked hydrogel.

In another example, the hydrophobic and hydrophilic components may be mixed thoroughly in a batch mixer or extruder, compatibilized with an amphiphilic polymer or copolymer (like polyethylene glycol or pluronic P123, and then the radioisotope component incorporated by using the low melting temperature of the biodegradable matrix, by hot press, injection molding or extrusion.

In some examples, the plurality of insoluble radio-isotope particles 3 may be provided by adding a precipitant to a plurality of radio-isotope particles. In one example, the plurality of radio-isotope particles 3 may comprise ions, so that the precipitant is added to a plurality of radio-isotope ions. In one example, the radio-isotope ions may be suspended in a solution to form a radio-isotope aqueous solution and disseminated throughout the carrier matrix 2. This makes the plurality of radio-isotope particles 3 in an insoluble form. In one example, the radio-isotope aqueous solution may be comprised of elements of the compound tetrasodium pyrophosphate. In other examples, any aqueous radio-isotope solution capable of being precipitated into a bioresorbable insoluble salt may be used. These include any aqueous solutions containing 32P phosphate ions, but other examples include but are not limited to radioactive calcium ions, radioactive chromium 51, radioactive Iodine ions (I-131, I-125, I-123 etc.), palladium 103, caesium [137] *131*, etc.

In one example, the precipitant comprises calcium chloride. In other examples, the precipitant may comprise a further aqueous solution of calcium ions, including the hydroxide or nitrate forms. The precipitant may comprise one or more of calcium chloride, calcium hydroxide, calcium nitrate or calcium bromide. In this way, the plurality of insoluble radio-isotope particles may be elements in the compound calcium pyrophosphate ($Ca_2P_2O_7$), anhydrous, dihydrate ($Ca_2P_2O_7.2H_2O$) or tetrahydrate (Ca2P2O7.4H2O).

The precipitant may also comprise any insoluble or poorly soluble salt capable of being bio-resorbed in the body. These include any variety of calcium phosphate or form of ammonium magnesium phosphate (Struvite). In one example, the functional groups of absorbable polymers may be iodinated using radioactive iodide 125 or 131, or crystalline iodide embedded/distributed throughout a bio-absorbable carrier matrix. In yet other examples, the precipitant may comprise another molecule containing calcium, magnesium, zinc or iron.

In other examples, the plurality of radio-isotopes 3 may be adsorbed into an anion exchange resin, and the precipitant may be applied after adsorption. In this example, a precipitant such as magnesium ammonium phosphate (Struvite) may be used. In another example, a gamma source such as chromium 51 may be precipitated in an anion exchange resin or into a resorbable radioactive molecule.

The microporous, hydrophobic substance with a hydrophilic surface may then be tuned through the addition of copolymers to achieve partial crystallization (semicrystalline). This is an advantage as it enables the device 1 to be flexible, compliant and conform to the shape of the wound site. The semicrystalline blend may modify the long hydrolysis degradation time of pure PCL/polylactide. That is, the rate of degradation of the device 1 may be determined by modifying the crystallinity of the bioresorbable carrier matrix structure 2. In some examples, the rate of degradation of the device 1 may be based on the half-life of the plurality of radio-isotope particles 3 and through modification of the crystallinity. Therefore the device 1 is suitable for use in surgery.

The bioresorbable carrier matrix structure 2 may then be completely biodegradable within the body. As described above, this is an advantage of the device 1. It is also a further advantage that when such a device 1 is utilized in a potentially contaminated field the device 1 may prevent chronic infection. In some examples, the bioresorbable carrier matrix structure 2 is degradable by intracellular, extracellular and enzymatic processes present in the body, such as pyrophosphatase or circulating osteocyte progenitors and/or mature osteocytes. In some examples, osteoclast cells (or their circulating osteoclast precursors) may degrade the structure 2. The osteoclast cells may degrade, resorb, modify and/or replace any of the entire family of calcium phosphate. This may include any insoluble and bioresorbable compound molecule. In other examples, the bioresorbable carrier matrix structure 2 is degradable by other enzymes present in the body.

In some examples, iodinated compounds may be used as the radio-isotope particles 3. This may comprise iodinating one or more functional groups of absorbable polymers using radioactive iodide, such as Iodine-131, Iodine-125 or Iodine-123. In other examples, crystalline iodide may be implanted into bioabsorbable polymers.

In this way, over time, the initially insoluble phosphate compounds in the plurality of insoluble radio-isotope particles may be made aqueous through the enzymatic processes of the body. The initially insoluble phosphate compounds present in the plurality of insoluble radio-isotope particles may be required for safe surgical handling as a sealed source of brachytherapy. The radio-isotope particles/ions may then diffuse from the bioresorbable carrier matrix structure 2 towards the wound site 100 to be absorbed intra-cellularly. The radio-isotope particles/ions may then be taken up into cancer cell DNA to increase apoptosis.

In some examples, the bioresorbable carrier matrix structure 2 may be pressed, extruded or injection molded into a desired shape, such as a flat sheet. The bioresorbable carrier matrix structure 2 may have a thin mesh surface interface.

The bioresorbable carrier matrix structure 2 comprises opposite first surface and second surfaces 21, 22.

In some examples, the plurality of radio-isotope particles 3 may be impregnated in a space between the bioresorbable carrier matrix structure 2 and hydrophilic substrate 4. For example, there may be a receptacle formed by at least two layers to receive the plurality of radio-isotope particles 3. In this example, a sealed source of radiotherapy may be obtained through the lamination of radioactive particles with hydrophobic or partially hydrophobic layers. In this way, the laminated radioactive particles may be capable of being completely or mostly bio-resorbed by the processes of the body that the device 1 is placed in. In other examples, insoluble radio-isotope particles, or a microporous matrix (like an ion exchange resin) containing insoluble radioisotope particles, may be imprinted into the surface of the bioresorbable carrier matrix structure 2.

A further advantage of the device is that since the plurality of radio-isotope particles 3 are embedded within the bioresorbable carrier matrix 2, safe removal of the device 1 (and thus the source of radio-isotope) is possible whilst maintaining the unidirectional shield if a return to theatre is required for management.

Hydrophilic Substrate 4

Figure 3:
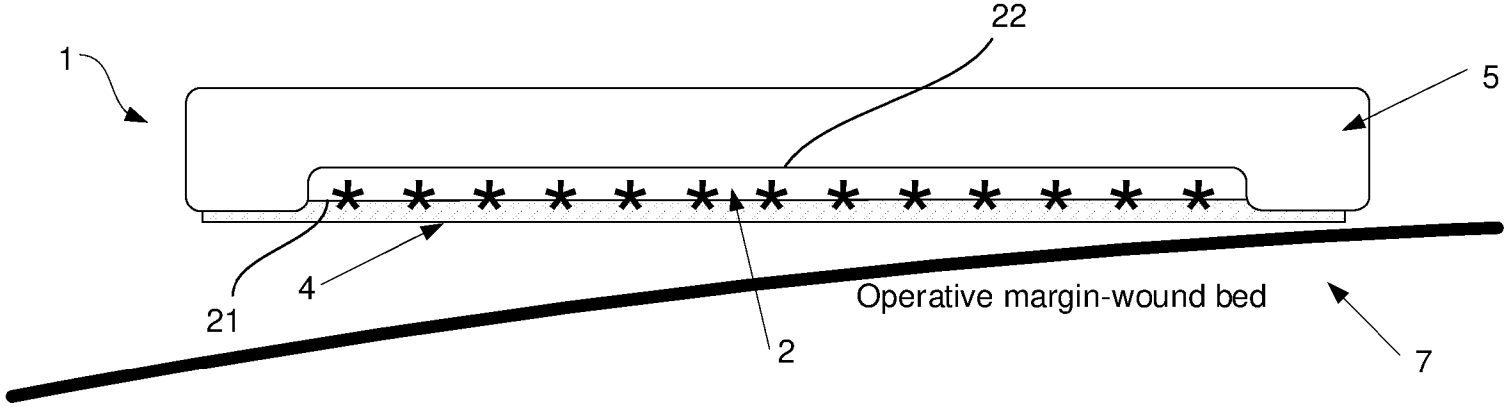
FIG. 3 illustrates a cross-sectional schematic representation of a brachytherapy device.

As described above, the device 1 further comprises a hydrophilic substrate 4 located adjacent to the first surface 21 of the bioresorbable carrier matrix structure. The hydrophilic substrate 4 faces the wound site and also adheres to the wound site 100. In this way, the hydrophilic substrate 4 provides integration, or crosslinking, of the device 1 to the wound site. In some examples, the hydrophilic substrate 4 is at, and across, the first surface 21 of the bioresorbable carrier matrix structure. This is illustrated in FIG. 3.

In one example, the hydrophilic substrate 4 is supplied in a fully hydrated state, at a similar equilibrium water content to the hydrogel substrate 5. In this way, the fully hydrated hydrophilic substrate 4 may be unlikely to undergo a dramatic change in size and/or modification in shape upon implantation and crosslinking to the tissues of the wound site 100. In another example, the hydrophilic substrate 4 may comprise a portion of substances required to create amide bonds and/or hydrogen-hydrogen interactions between the device and tissues of the wound site 100 in the body. In this way, an additive substance may activate the crosslinking between the device and the tissues, such as 1-Ethyl-3-(3-dimethylaminopropyl) carbodiimide (EDC), dopa, or other crosslinking agent.

In some other examples, the hydrophilic substrate 4 absorbs moisture from the wound site to allow wetting and gelation of the hydrophilic substrate 4 to conform to the wound site. The hydrophilic substrate 4 may be selected to be relatively rapidly absorptive, allowing close conformation of the device 1 to the wound site. In other examples, the hydrophilic substrate 4 may be configured to be absorbed at the wound site within three to five days.

The hydrophilic substrate 4 is configured to degrade, when implanted at the wound site 100, at a rate shorter than the bioresorbable carrier matrix structure to prevent migration of the device during the half-life of the plurality of radio-isotope particles 3. This ensures that the device 1 does not move from the wound surface 100. That is, the hydrophilic substrate 4 is configured to absorb at a faster rate than the bioresorbable carrier matrix structure 2. This allows the plurality of radio-isotope particles 3 to be maintained in place at the wound site until it is no longer substantially active 4. In some examples, the time to substantial inactivity of the radio-isotopes may be between 9 to 28 days.

Figure 2:
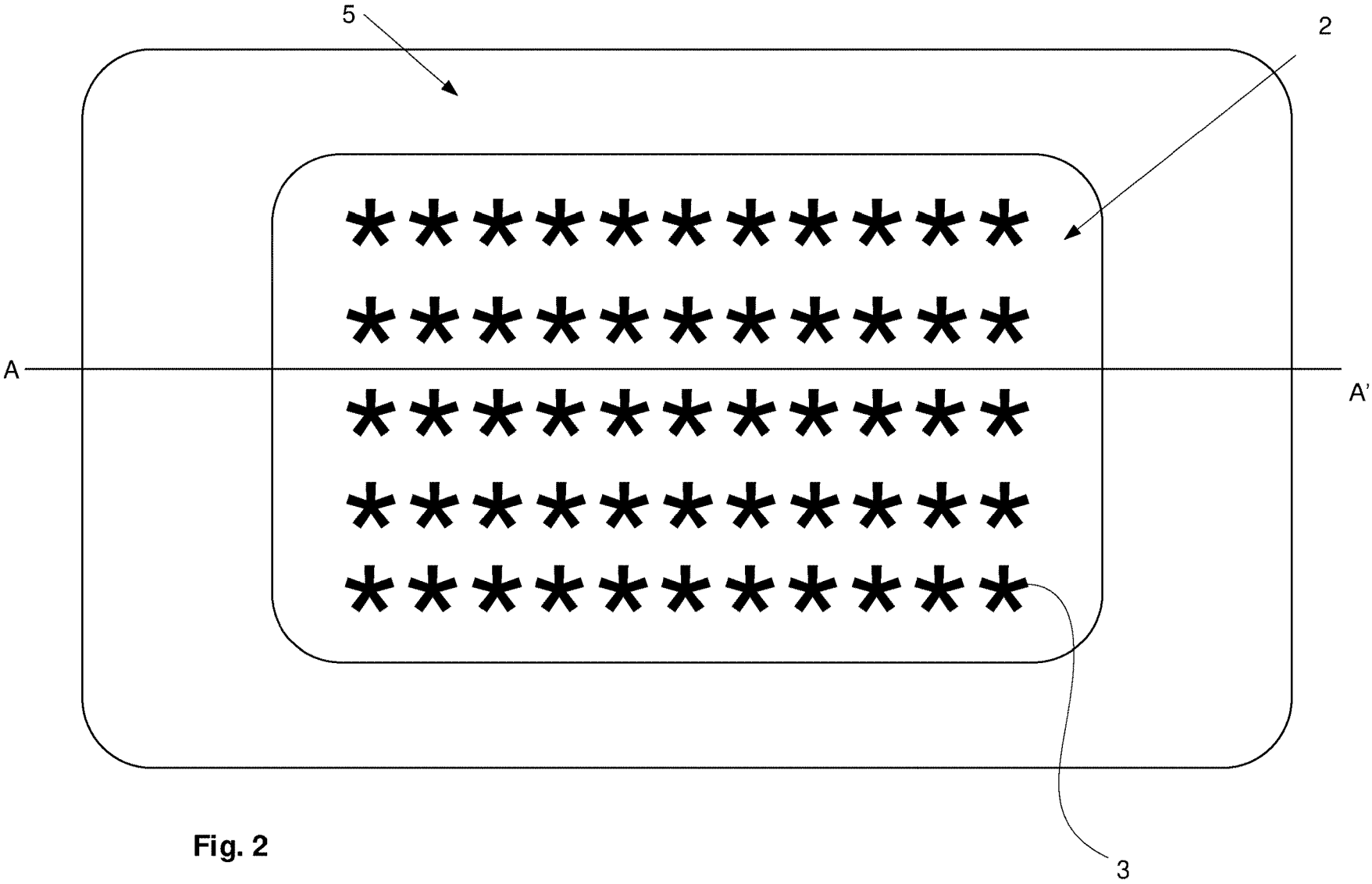
FIG. 2 illustrates a further schematic representation of a brachytherapy device, following absorption of a hydrophilic substrate.

FIG. 2 illustrates an example of device 1 showing faster absorption of the hydrophilic substrate 4. As shown, the hydrophilic substrate 4 has completely absorbed. The hydrogel substrate 5, bioresorbable carrier matrix structure 2 and the plurality of radio-isotope particles 3 remain in place at the wound site.

Figure 4:
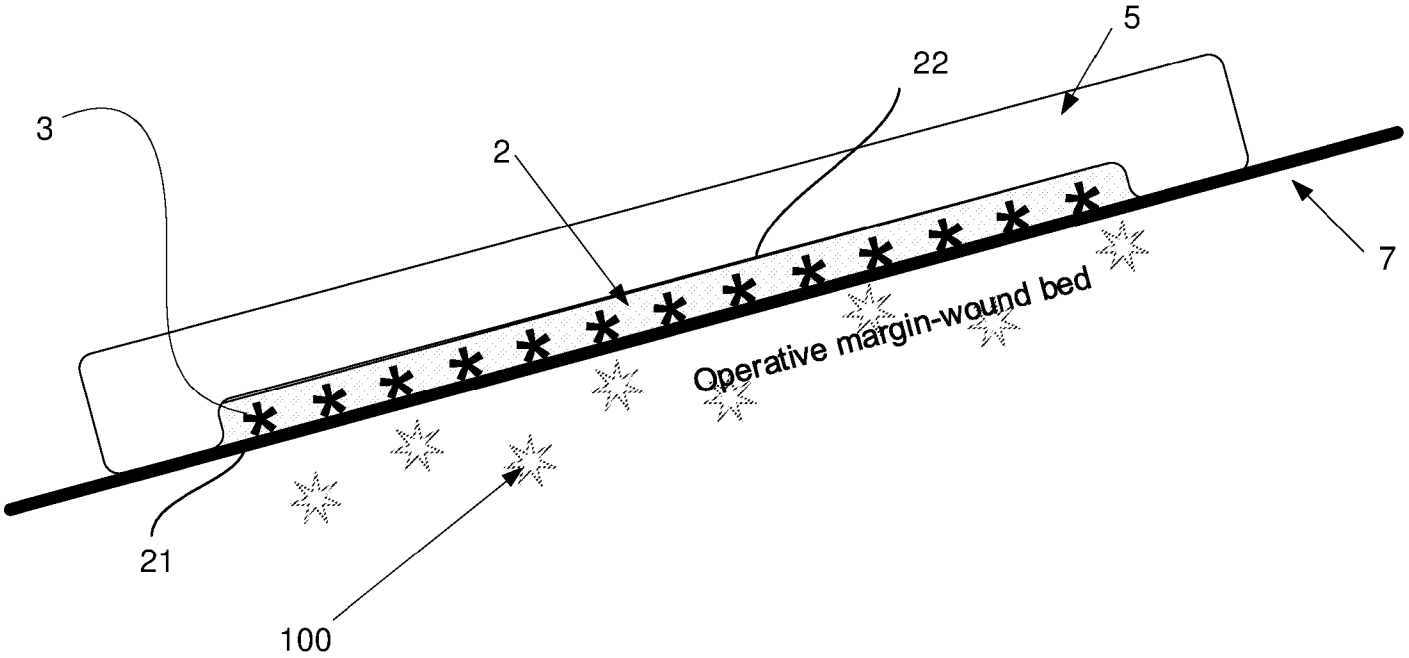
FIG. 4 illustrates a further cross-sectional schematic representation of a brachytherapy device, following absorption of a hydrophilic substrate.

FIG. 4 illustrates a cross-sectional view showing the hydrophilic substrate 4 being absorbed into the wound site. In this example, the hydrogel substrate 5, bioresorbable carrier matrix structure 2 and the plurality of radio-isotope particles 3 remain in place at the wound site 100.

The hydrophilic substrate 4 may be comprised of a crosslinked polymer. In some examples, the hydrophilic substrate 4 also comprises one or more of: any variety of) starch, carboxymethyl cellulose, glycerol, xylitol, or citric acid, or any variety thereof. In other examples, the hydrophilic substrate 4 may comprise other surgical adhesive substances, such as carbodiimide crosslinking, dopa-lysine interactions, or citric acid crosslinking.

In other examples, the hydrophilic substrate 4 may comprise a thin layer of bio-compatible resin, gel, or flexible biopolymer such that it absorbs water rapidly to conform with the operative bed. Other polymers derived from cellulose may also be used.

The hydrophilic substrate 4 may also comprise a radio-sensitizing agent, such as gemcitabine or capecitabine. The radio-sensitizing agent may be suspended in the hydrophilic substrate 4 by a solvent casting technique, solution immersion, or melt extrusion technique. In this way, when the wound site absorbs the hydrophilic substrate 4 the radio-sensitizing agent may release. This may have the effect of making tumor cells that are in or close to the wound site susceptible to radiation from the plurality of radio-isotope particles 3.

The hydrophilic substrate 4 hydrates once applied to the wound site to form a surface film which conforms to the wound site. As illustrated in FIG. 3 the hydrophilic substrate 4 may extend beyond the edges of the bioresorbable carrier matrix structure 2.

In some examples, the hydrophilic substrate 4 provides a concomitant haemostatic effect on the wound site, preventing haematoma which may lift the device 1 away from the wound site. In this example, the hydrophilic substrate 4 may further comprise a coating or suspension of a haemostatic agent, such as thrombin, fibrin, fibrinogen or other haemostatic agents to augment the haemostatic properties of the hydrophilic substrate 4.

Hydrogel Substrate 5

The device 1 further comprises a hydrogel substrate 5 located adjacent to the second surface 22 of the bioresorbable carrier matrix structure 2. The hydrogel substrate 5 enables conformability, flexibility and the ability to allow surgical implantation of the device 1. The hydrogel substrate 5 is configured to shield radioactivity and to degrade at a rate longer than the half-life of the plurality of radio-isotope particles. The hydrogel substrate 5 may also be configured to fully hydrolyze at a rate longer than the half-life of the plurality of radio-isotope particles. In this way, the hydrogel substrate 5 is configured to absorb any emitted radiation to protect surround tissues of the patient and, in some circumstances the operator of the device 1, such as a surgeon. This is an advantage of the device 1 as the shield provided by the hydrogel substrate 5 assists in the device being unidirectional, unlike devices of the prior art as described above.

In one example, the hydrogel substrate 5 is attached to the second surface 22 of the bioresorbable carrier matrix structure 2 so that the hydrogel substrate 5 is adherent to and integrated in a hydrated state using phosphate buffered saline (or other biocompatible solution). The hydrated state may mean that the hydrogel substrate 5 is at or close to its equilibrium water content (EWC). This is an advantage to the device because the device 1 is convenient and safe for application during surgery, unlike devices of the prior art. That is, the device may be safely handled from its packaging as unidirectional and does not require additional assembly by the operator of the device.

In some examples, the hydrogel substrate 5 limits penetration of the plurality of radio-isotope particles 3 to a few millimeters. As illustrated in FIGS. 3 and 4 the hydrogel substrate 5 faces away from the wound site 100. Furthermore, in some examples, the hydrogel substrate is at, and across the second surface 22 of the bioresorbable carrier matrix structure. In further examples, as illustrated in FIGS. 1 to 4, the hydrogel substrate 5 extends beyond a perimeter of the bioresorbable carrier matrix structure 2. This provides additional shielding to tissue near the perimeter regions. As illustrated in FIG. 3, the hydrogel substrate 5, near the perimeter, may be in contact with the hydrophilic substrate 4. Thus, in some examples, the bioresorbable carrier matrix structure is encapsulated by the hydrogel substrate 5 and the hydrophilic substrate 4 when the device 1 is first implanted.

The hydrogel substrate 5 may be combined with the bioresorbable carrier matrix structure 2 by at least one of: mechanical integration, chemical crosslinking or enzymatic crosslinking. In some examples, a combination of mechanical integration and chemical crosslinking with 1-Ethyl-3-(3-dimethylaminopropyl) carbodiimide (EDC) and/or N-Hydroxysuccinimide (NHS) carbodiimide chemistry may be used. In this example, surface modification may be required for example by way of plasma treatment and/or surface hydrolysis.

The hydrogel substrate 5 may be composed of a hydrophilic polymer interpenetrating multi-polymeric hydrogel. This may contain polyvinyl alcohol, carboxymethylcellulose, partially hydrolyzed collagen and xylitol, crosslinked with citric acid. The hydrogel substrate 5 may also comprise a blend of copolymer using polyethylene glycol. In some examples, a catalyst such as titanium dioxide may be present for the citric acid crosslinking. In yet other examples, other hydrophilic resorbable polymers or sugar alcohols may be used, including but not limited to sodium alginate, starch, chitosan, forms of cellulose, varieties or collagen, polyethylene glycol, glycerol, sorbitol and the like.

As described above, the hydrogel substrate may comprise, at least in part, citric acid. A percentage of citric acid may be selected to specify the rate that the hydrogel substrate 5 degrades to maintain structural integrity and shielding capacity. In some examples, the percentage of the citric acid may be between 2.5% and 10%. In this way, the citric acid ensures that the hydrogel substrate 5 continues to shield radiation for a duration of time after implantation at the wound site. This may be useful, for example, if the patient with such a device 1 is required to return to theatre at a time after implantation. In other examples, chemical crosslinking may be performed with an agent such as glutaraldehyde, or crosslinked with gamma irradiation, UV exposure or through a freeze-thaw method.

The hydrogel substrate 5 may have a thickness of at least 3 mm, and preferably closer to 3.5 mm. In other examples, a gamma source may be used which may necessitate an increased thickness of the hydrogel substrate 5 to provide an effective unidirectional shield. As illustrated in FIG. 3, the hydrogel substrate 5 may be configured to have a central recessed portion for receiving the bioresorbable carrier matrix structure 2 within.

The hydrogel substrate 5 may also act to prevent damage or undesired attachment and adhesions of surrounding tissues and structures to the device. As illustrated in FIG. 3, the hydrogel substrate 5 may be attached at edge portions to the hydrophilic substrate 4. In this way, the hydrogel substrate 5 may extend beyond edges of the first and second surfaces 21, 22 of the biocompatible carrier matrix structure 2.

Method 200 of Manufacturing a Flexible Brachytherapy Device

Figure 11:
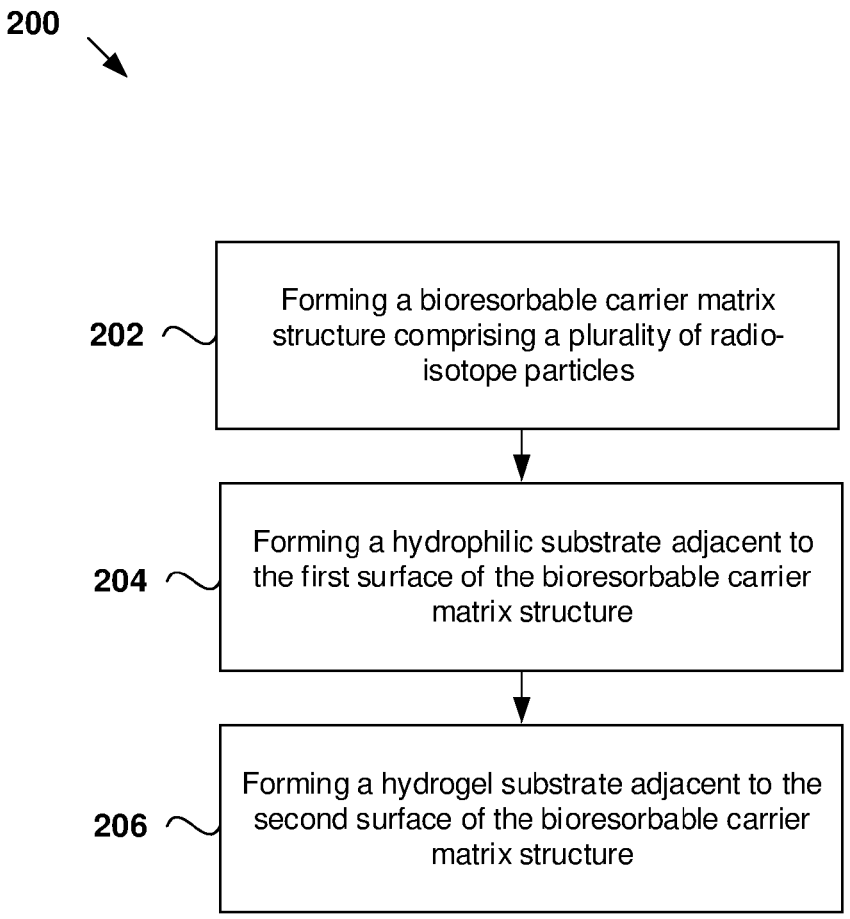
FIG. 11 illustrates a method for manufacturing a brachytherapy device.

As illustrated in FIG. 11 there is also provided a method 200 of manufacturing a flexible brachytherapy device for application on a wound site in a body. The method 200 comprises forming 202 a bioresorbable carrier matrix structure 2 comprising a plurality of radio-isotope particles 3. In the method 200, the bioresorbable carrier matrix structure 2 may be provided by adsorbing a plurality of insoluble radio-isotope particles to a microporous, hydrophobic substance with a hydrophilic surface 4 to provide the bioresorbable carrier matrix structure 2 as described above. In some examples, the bioresorbable carrier matrix structure 2 may be formed using a thermoplastic process, such as a combination of extrusion and/or heated batch mixing. In other examples, injection molding or hot press may be used. In some examples, the plurality of insoluble radio-isotope particles is provided by adding a precipitant to the plurality of radio-isotope particles.

The bioresorbable carrier matrix structure 2 is configured to degrade at a rate substantially longer than a half-life of the radio-isotope particles 3 such that activity from the plurality of radio-isotope particles 3 is localized to the wound site, wherein the biodegradable carrier matrix structure 2 has opposite first surface and second surfaces 21, 22.

The method 200 further comprises forming 204 a hydrophilic substrate 4 adjacent to the first surface 21 of the bioresorbable carrier matrix structure 2, wherein the hydrophilic substrate 4 adheres to the wound site. The hydrophilic substrate 4 is configured to degrade, when implanted at the wound site, at a rate shorter than the bioresorbable carrier matrix 3 to prevent migration of the device 1 during the half-life of the plurality of radio-isotope particles 3. The hydrophilic substrate may be formed through extrusion, solvent casting, spray coating and/or dipping.

The method 200 further comprises forming 206 a hydrogel substrate 5 adjacent to the second surface 22 of the bioresorbable carrier matrix structure 2, the hydrogel substrate 5 configured to shield radiation and to degrade at a rate longer than the half-life of the plurality of radio-isotope particles 3. In some examples, the hydrogel substrate 5 may be formed through a combination of multiple polymers prior to melt extrusion or solvent casting.

The hydrophilic substrate 4 and hydrogel substrate 5 may be adhered to the device 1 through one or more of the techniques of mechanical integration, hot press, mold, chemical and/or enzymatic crosslinking. This may comprise carbodiimide chemistry, GEM, transglutaminase, or other more traditional method of crosslinking (e.g., Gluteraldehyde). In one example, a combination of mechanical integration and carbodiimide chemistry is used, utilizing amide-hydroxyl bonds between the collagen molecules in the radioactive bioresorbable carrier matrix structure 2 and free amide and/or hydroxyl groups in the hydrophilic substrate 5 and hydrogel substrate 5.

Applicator Device

Figure 6:
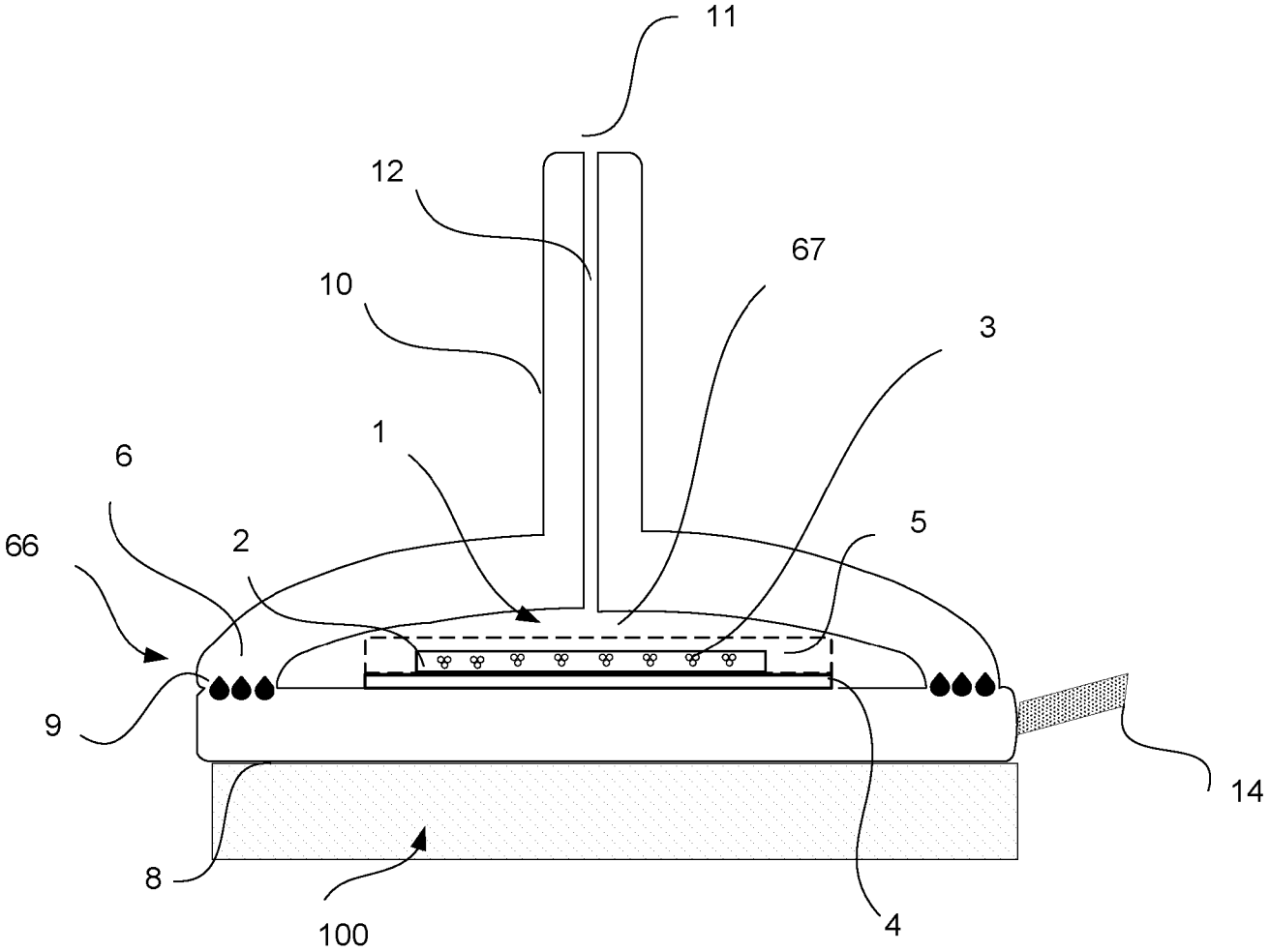
FIG. 6 illustrates a schematic representation of an applicator device.

FIG. 6 illustrates an example of an applicator device 66 for application of a brachytherapy device 1 to a wound site 100 in a body. The applicator device 66 provides for application of the brachytherapy device 1 to a wound site 100 while protecting the operator, such as a surgeon, or nuclear medicine physician. The applicator device 66 also provides for safe distribution and storage of the device 1, as well as for ready location of the device 1 at the wound site 100. The applicator device 66, when used together with the brachytherapy device 1 contained therein, keeps the brachytherapy device 1 dry and also shields any nearby personnel from radioactive radiation. This minimizes collateral radiation exposure.

The applicator device 66 is configured to be placed inside the body so that the base 8 faces away from the operator and towards the wound site 100.

The applicator device 66 comprises an upper housing 6 having a recess 67 to receive a brachytherapy device 1. The upper housing 6 of the applicator device 66 may comprise a transparent, semi-transparent, or translucent material to allow the surgeon to accurately place the brachytherapy devices whilst shielding the surgeon from beta radiation. In some examples, the upper housing 6 may be formed of an acrylate polymer, such as acrylic (Perspex).

Figure 12:
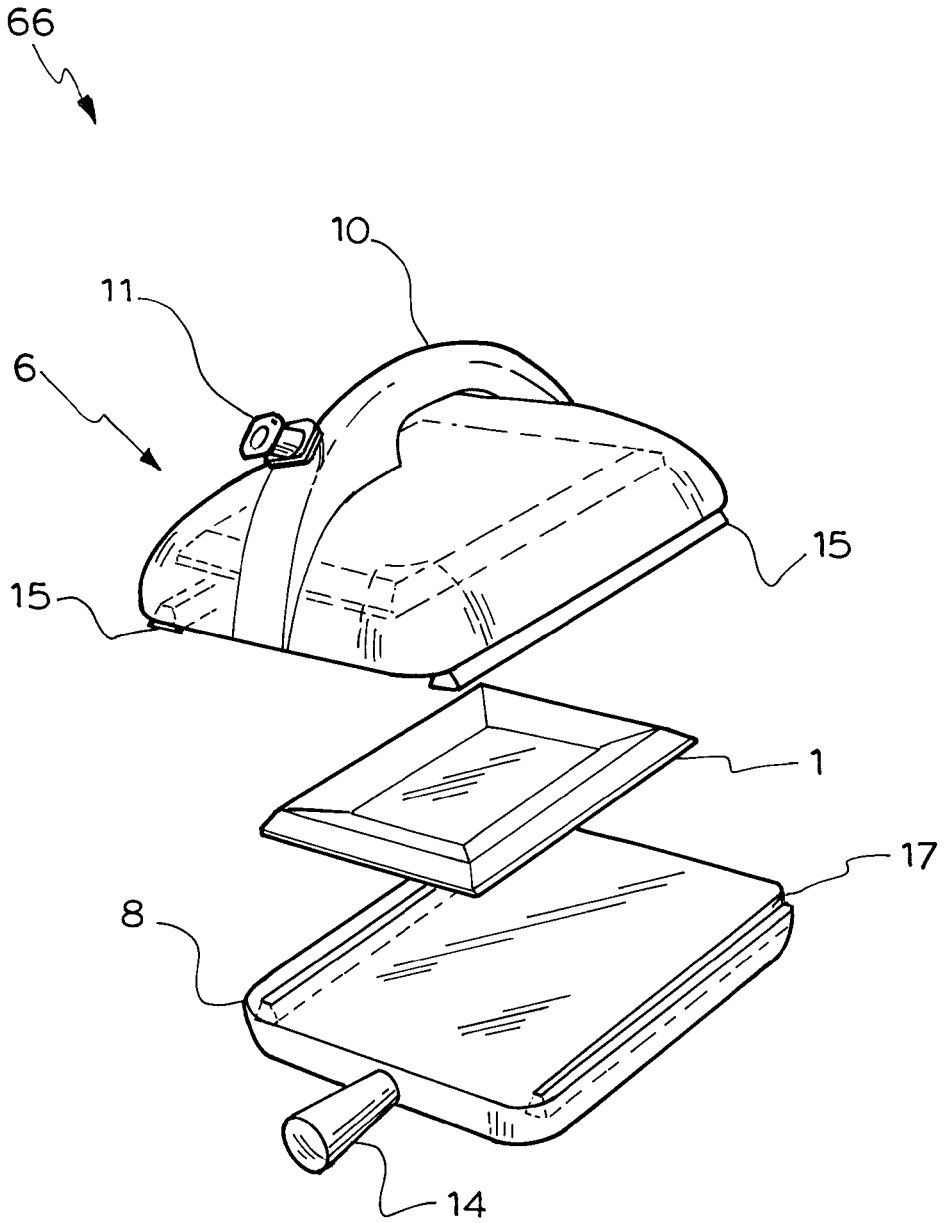
FIG. 12 illustrates a further schematic of an applicator device.

The applicator device 66 also comprises a removable base 8 attached with the upper housing 6, wherein when attached the removable base 8 and upper housing 6 shield radiation from the brachytherapy device 1. In some examples, the removable base 8 is slidably attached with the upper housing 6. In this way, the removable base 8 may be slidably removable from the upper housing 6. As illustrated in FIG. 12, in some examples, the upper housing 6 comprises rails 15 that are received by, and engage with, grooves 17 on the removable base 8. In some examples, this may include rails 15 that are shaped to dovetail with the grooves 17. It is to be appreciated that other sliding engagement arrangements may be used, such as inwardly facing and opposing grooves that receive opposing edges of a base.

The removable base 8 may have a planar surface. The removable base 8 may be comprised of a material suitable for protection against Bremsstrahlung radiation, such as acrylic. In another example, if a gamma emitter was used, lead vinyl, lead containing glass or lead containing vinyl-acrylic may be employed in the removable base 8. The combination of the upper housing 6 and removable base 8 provides safe handling and delivery of the brachytherapy device 1 to the wound site 100 during and after placement during surgery.

The removable base 8 may be configured to face a first surface 21 of the brachytherapy device 1. In some examples, the removable base 8 may face a hydrophilic substrate 4 of the brachytherapy device 1 in accordance with the examples described above.

Figure 13:
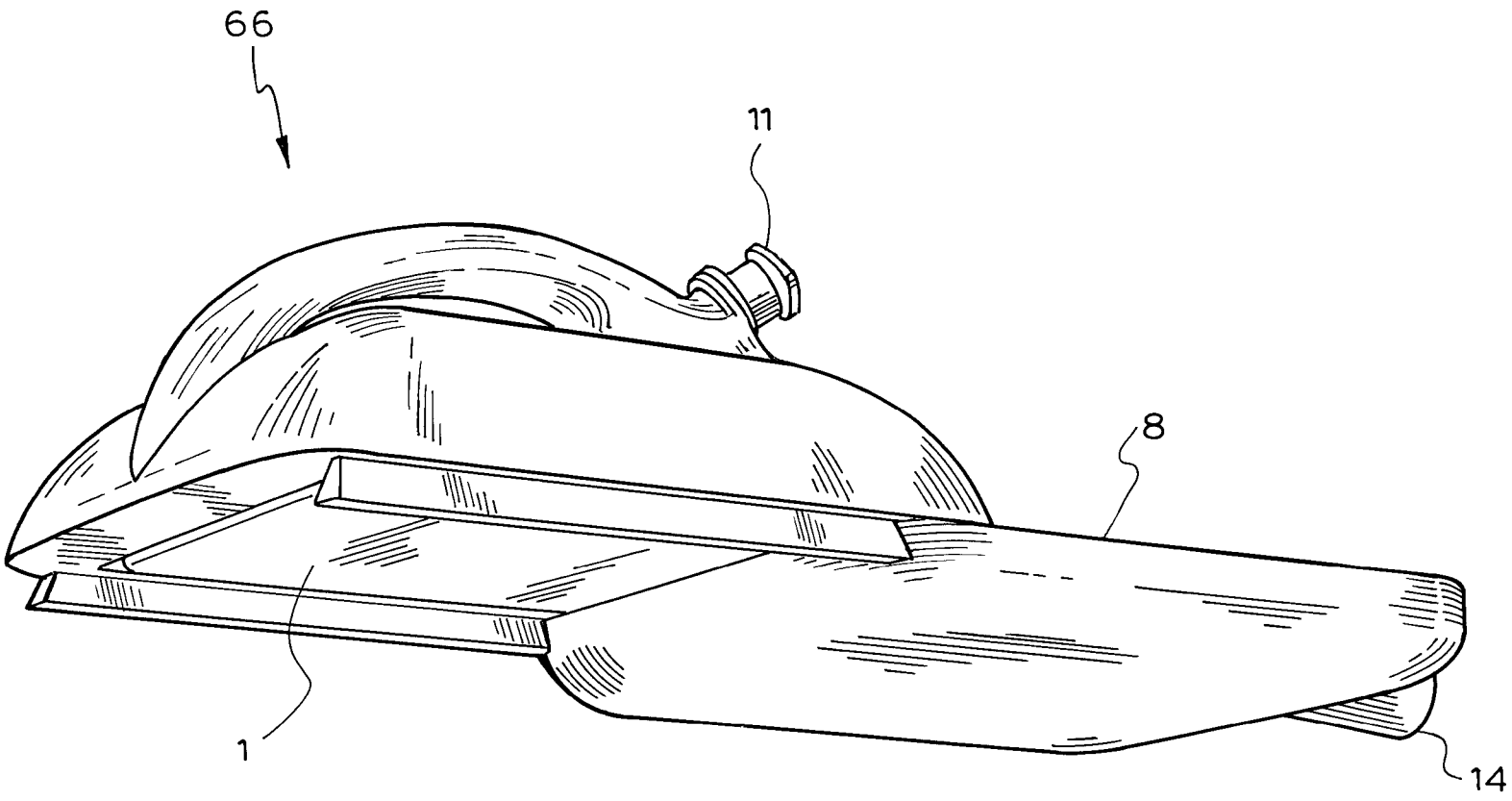
FIG. 13 illustrates a further schematic of an applicator device.
Figure 14:
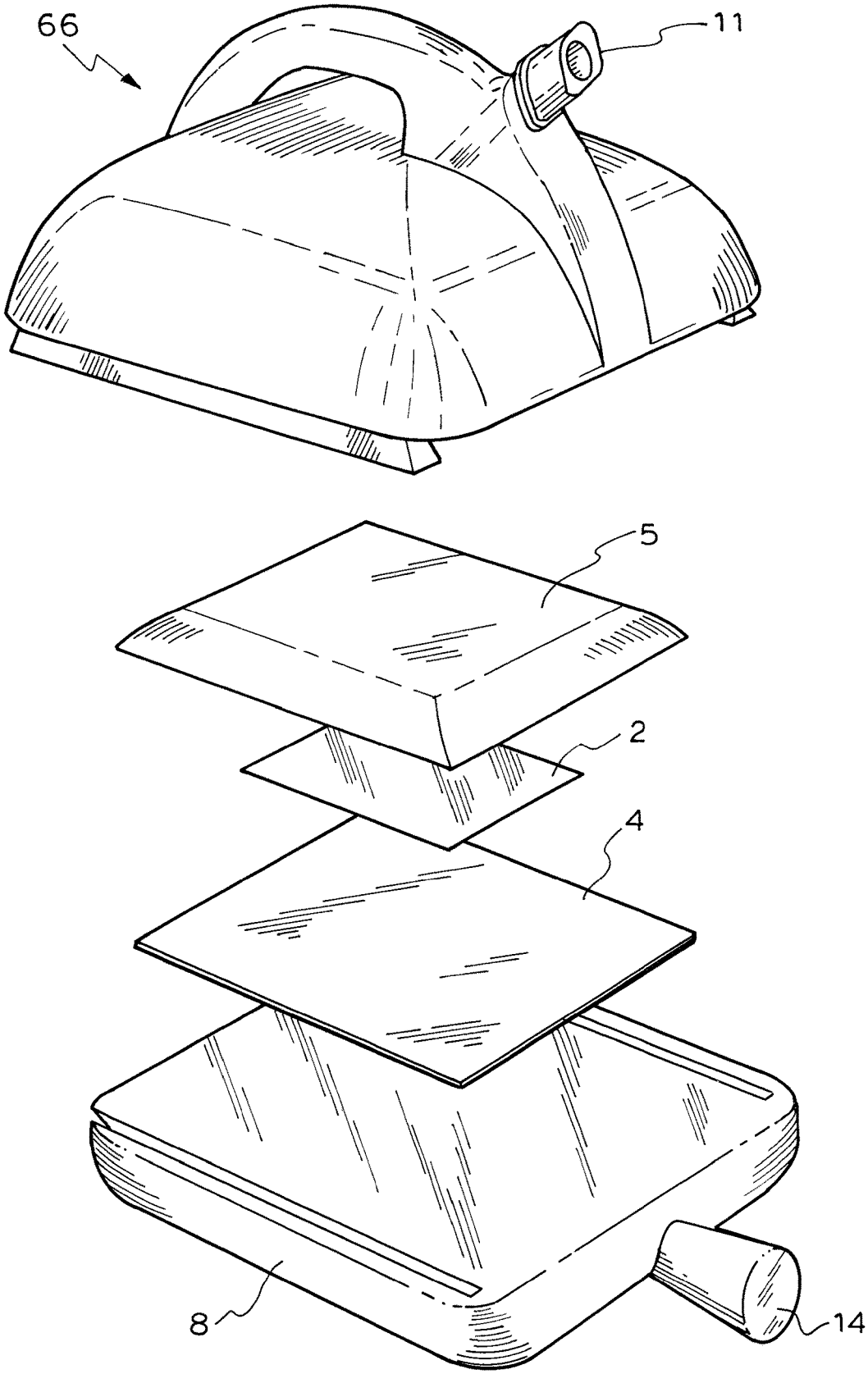
FIG. 14 illustrates a further schematic of an applicator device.

The removable base 8 is removable, such as slidably removable, from the upper housing 6 to expose a first surface 21 of the brachytherapy device 1 to a wound site 100. FIG. 13 illustrates a slidably removable base 8. The removable base 8 may also be removable by other means such as a hinge associated with the applicator device 66. In some examples, the first surface 21 may comprise a hydrophilic substrate 4 of the brachytherapy device 1 as described above. This is illustrated in FIG. 14. In this way, the removable base 8 is slidably removed during application and location of the brachytherapy device 1 to the wound site 100 to expose the hydrophilic substrate 4 to the wound site 100.

The removable base 8 may also comprise a tab 14 to allow an operator, such as the surgeon, to apply a pulling or pushing force to slidably remove the base 8 from the upper housing 6 and to therefore expose a first surface 21 of the brachytherapy device 1 so that the device 1 may be adjacent to and conform to the wound site 100.

In some examples, the upper housing 6 further comprises an inlet port 11 fluidly connected to the recess 67. The inlet port 11 allows introduction of a fluid through the inlet port 11 to the brachytherapy device 1 in the recess 67. In some examples, a channel 12 is connected to the inlet port 11 for the fluid to flow from the inlet port 11 to the brachytherapy device 1 in the recess 67. This may include introducing a liquid to hydrate the hydrogel substrate 5.

In some examples, the inlet port 11 may be used to 'activate' an adhesive component of the brachytherapy device 1, either by channeling an adhesive substance to an attachment surface of the device 1, or some component of a crosslinking solution, which on attachment to the tissues of the wound site 100 provides crosslinking between the device 1 and the tissues of the wound site 100. Such agents may incorporate one component of carbodiimide chemistry (e.g., 1-Ethyl-3-(3-dimethylaminopropyl) carbodiimide (EDC)), or facilitate dopa-lysine interactions with or without the facilitation of transglutaminase.

The applicator device 66 may further comprise a soluble adhesive 9 to additionally secure the upper housing 6 and the removable base 8. In this way the soluble adhesive 9 provides an additional security against shielding the operator of the applicator device 66 from any activity from the brachytherapy device 1 contained therein. The soluble adhesive 9 may also provide a seal, such as a hermetic seal, for the applicator device 66.

The soluble adhesive 9 may be a water and/or heat soluble glue. The soluble adhesive 9 may be dissolvable by a liquid 13 introduced into the recess 67 to allow the removable base 8 to be slidably removed from the upper housing 6. In some examples, the upper housing 6 and removable base 8 may be adhered by the soluble adhesive 9 about the periphery portions of the upper housing 6 and removable base 8.

In some examples, water may be injected into the inlet port 11 of the upper housing 6. In this way the soluble adhesive 9 may be solubilized to an extent so that the removable base 8 may be removed to expose the first surface 21 (such as the hydrophilic substrate 4) of the brachytherapy device 1 to the wound site 100.

In other examples, heat in addition to a liquid may be inserted in the inlet port 11 to the recess 67. For example, this may comprise warm water. In this way the soluble adhesive 9 may absorb the heated liquid so that the soluble adhesive 9 is solubilized to remove the removable base 8 to expose the hydrophilic substrate 4 of the brachytherapy device 1 to the wound site 100. In a further example, a hydrogel substrate 5 of the brachytherapy device 1 may also absorb the heat and/or liquid to fill and expand. The hydrogel substrate 5 shields radioactivity as described above.

In one example, after the applicator device 66 is located at the wound site 100 water and heat may be inserted in the inlet port 11 to the recess 67. The soluble adhesive 9 may absorb the water and heat. The hydrophilic substrate 4 of the device 1 may also absorb the water and heat. The hydrogel substrate 5 may also absorb the water and heat. The bioresorbable carrier matrix structure 2 may also absorb the water and heat. When the hydrogel substrate 5 is fully absorbed, the saturated hydrogel substrate 5 is readily detached from the upper housing 6 for application of the device 1 to the wound site 1. The device 1 may then become flexible and conform and adhere to a surface such as the wound site 100. The device 1 may then deliver radiation dosage.

In further examples, a liquid or gas suitable for sterilization may be inserted into the inlet port 11. For example, ethylene oxide may be introduced to sterilize the device 1 and/or applicator device 66 at a manufacturing facility and/or before surgery.

Figure 7:
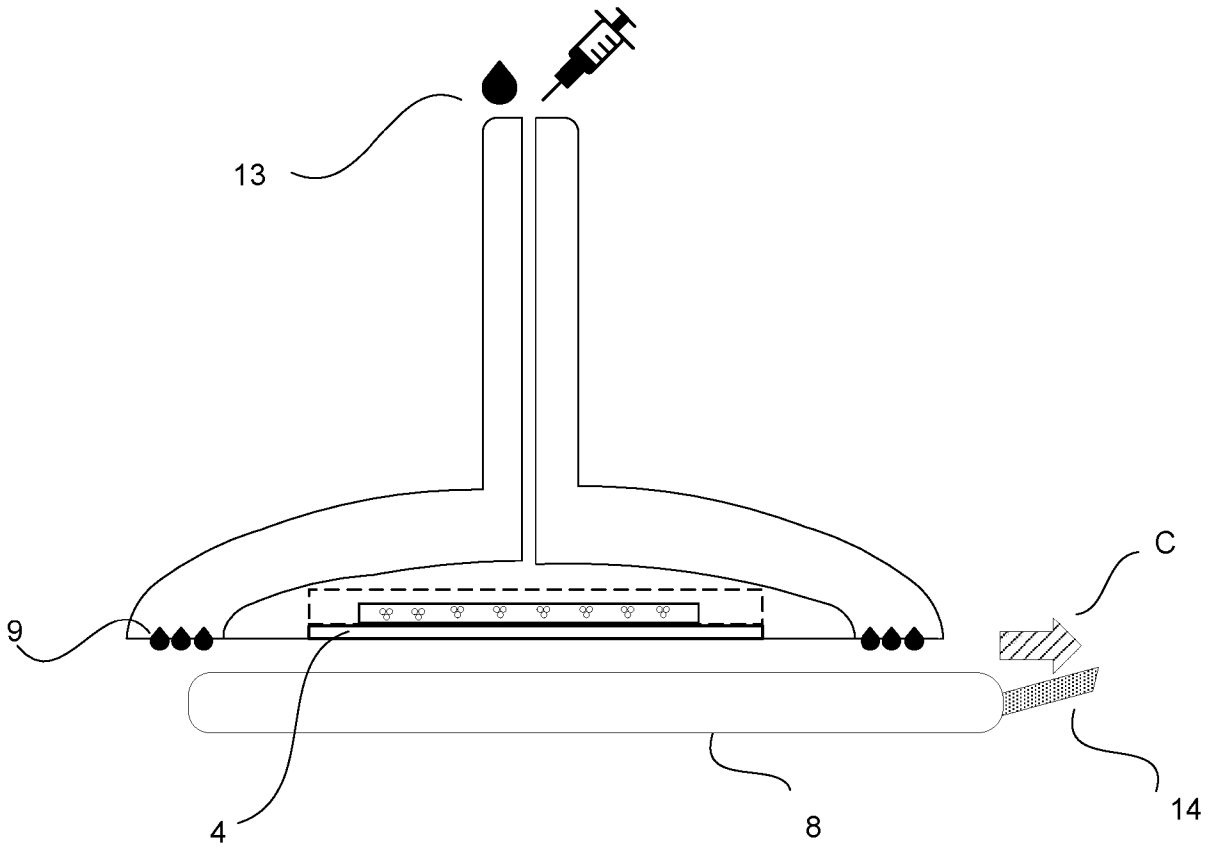
FIG. 7 illustrates a further schematic representation of an applicator device.

The applicator device 66 may further comprise a handle 10 at the upper housing 6 to assist placement of the applicator device 66 and brachytherapy device 1 to the wound site 100. In some examples, the handle 10 may be longitudinal as illustrated in FIGS. 6 and 7. In other examples, the handle 10 may be in another configuration attached to the upper housing 6.

In some examples, the device 1 may be completely surrounded by the upper housing 6 and removable base 8. That is, the hydrophilic substrate 4 and bioresorbable carrier matrix 2 may be smaller in diameter than the removable base 8 and the hydrogel substrate 5. In one example, the hydrophilic substrate and bioresorbable carrier matrix 2 may be 3 cm in diameter flat circular, and the removable base 8 and hydrogel substrate 5 may be 4 to 4.5 cm in diameter flat circular.

There is also provided a brachytherapy system comprising the applicator device 66 and device 1 as described above. In some examples, the hydrogel substrate 5 of the device 1 may be hydrated at equilibrium water content by the inlet port 11 of the applicator device 66. In this way, the hydrogel substrate 5 may be fully formed, hydrated and crosslinked with the device 1. It is an advantage that the device 1 may then be handled from the applicator device 66 by the operator without any additional assembly by the operator or associated staff. It is also an advantage that the fully hydrated hydrogel substrate 5 shields radioactivity from the operator, thus rendering the radiation from the device 1 substantially unidirectional.

Variations

Figure 8:
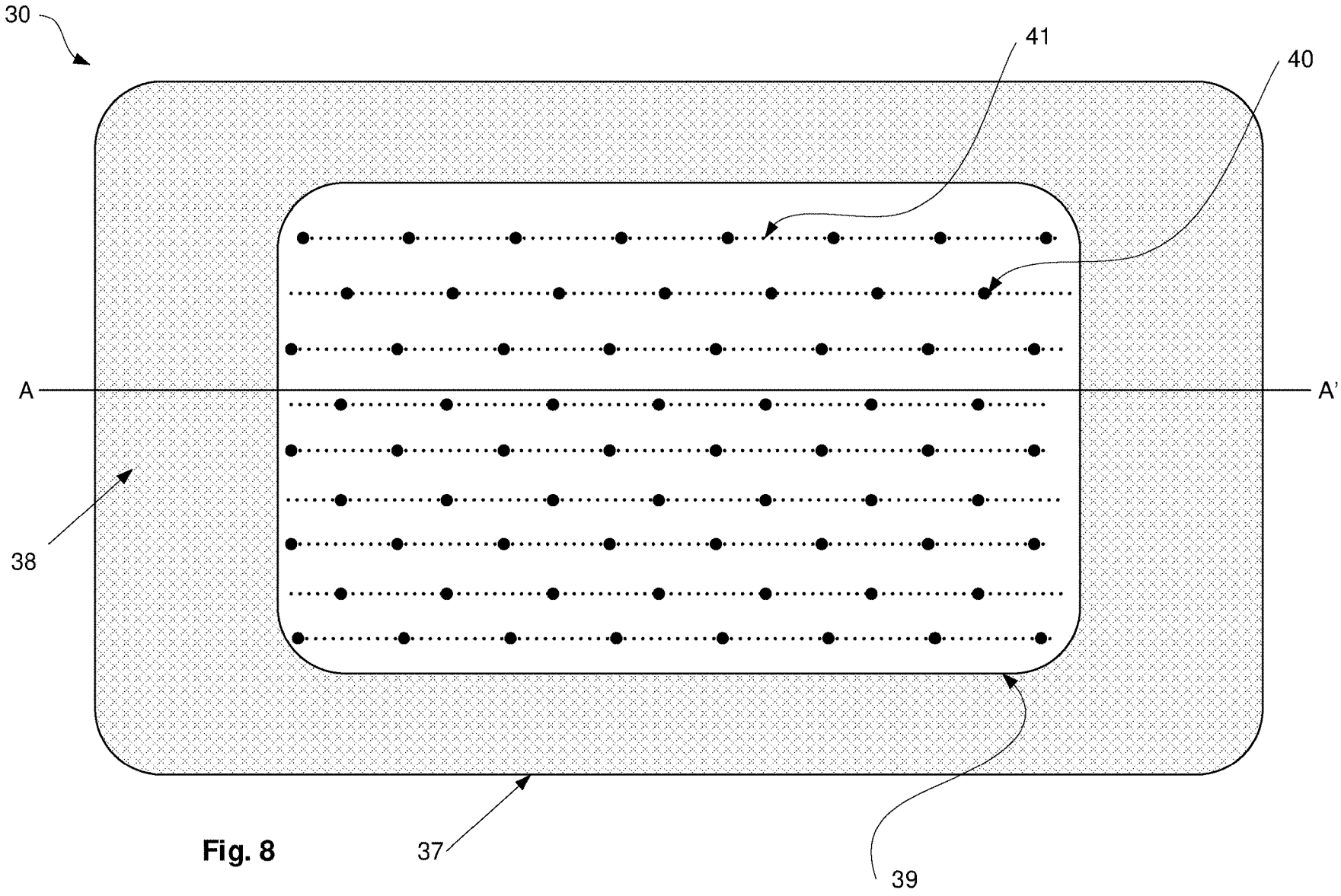
FIG. 8 illustrates a further schematic representation of a brachytherapy device.
Figure 9:
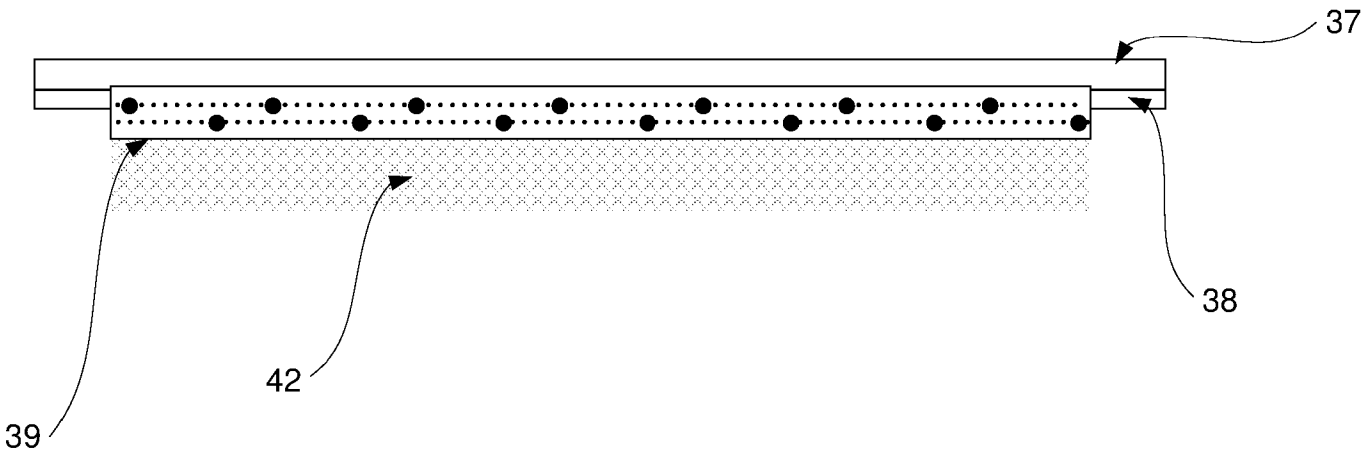
FIG. 9 illustrates a cross-sectional schematic representation of the device in FIG. 8.
Figure 10:
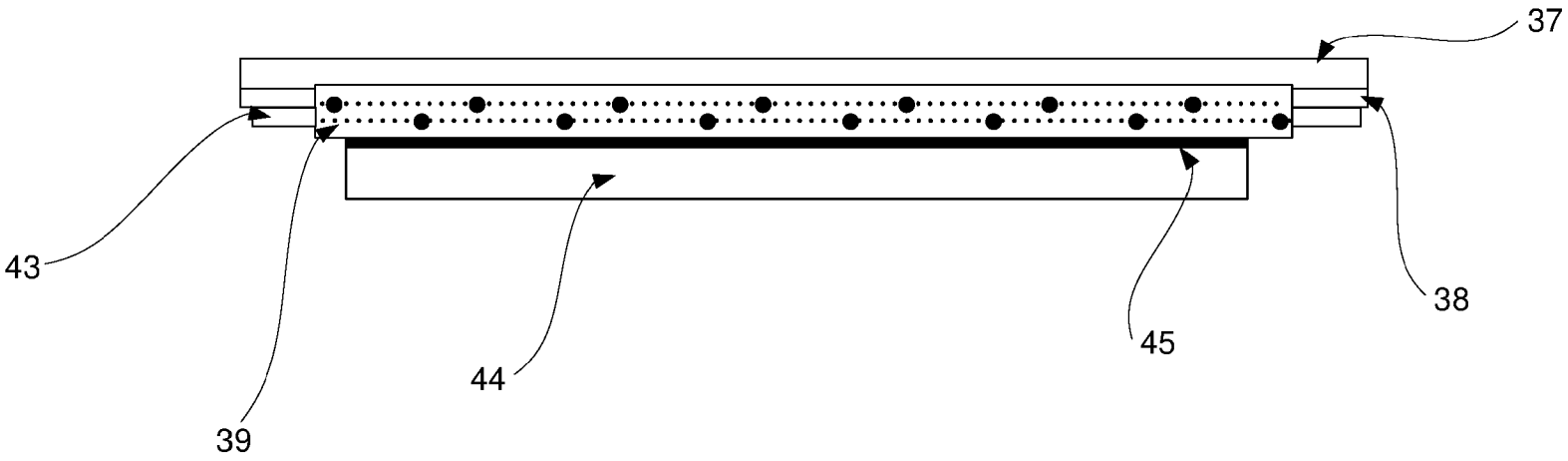
FIG. 10 illustrates a further schematic representation of a brachytherapy device.

In a further example referring to FIGS. 8 to 10, there is shown a substantially planar topical brachytherapy laminate structure 30 comprising an outer film 37 made from a polycaprolactone-starch composite, an inert adhesive layer 38 comprising carboxymethylcellulose overlaying a part of the outer film, and an active radioisotope film layer 39 comprising a predetermined ratio of 32P particles 40 and 33P particles 41, in a carboxymethylcellulose matrix. In this example, the inert adhesive layer 38 extends about the active radioisotope film layer 39 on or adjacent the peripheral edge of the outer film 37 and is adapted to contact a surface of a patient's skin to adhere the laminate structure to a desired location. In one aspect, the radioisotope particles may be impregnated in the surface interface between layer 45 and layer 39.

As shown in FIG. 10, the inert adhesive layer 38 may further include a peelable backing layer (removable film) 43 for storage which is peeled away to expose the inert adhesion layer for adhesion to a desired treatment site. In this embodiment the inert adhesive is a pressure sensitive adhesive layer 8 having removable backing film 43. The outer layer 37 may comprise a hydrogel layer adapted to absorb radiation to protect the surgeon and any other tissues while they finish the case and the radioisotope decays. In this embodiment the hydrogel layer 37 may have a thickness of between about 4 to 5 mm in order to absorb the radioactive particles.

Layers 45 and 39 are a smaller diameter (for example, 3 cm flat circle) than layers 44 and 37 (for example, 4 to 4.5 cm flat circle), so that it is completely surrounded by radioactive shielding.

In this example, the positive margin is focused in a small location, on a two-dimensional (albeit irregular) surface. Hence it is preferred that the example described by the laminate structure in FIGS. 8 and 9 is a substantially flat composite sheet with multiple layers.

Referring to FIG. 9, the laminate structure is shown located on a wound bed represented by reference numeral 42 with the active radioisotope film layer 39 directly contacting the wound bed. In FIG. 10, the planar topical brachytherapy laminate structure further includes a removable shielding sheet 44. In one example, the removable shielding sheet 44 may comprise a lead vinyl/acrylic composite that is present only for handling and delivery and removed on application.

The shielding sheet 44 is attached peripherally to the active radioisotope film layer 9 with water and/or heat soluble glue for peeling away therefrom for attachment to the wound bed. As further shown in FIG. 10, a thin film 45 of quick absorbing hydrocolloid such as cellulose may be sandwiched between the active radioisotope film layer 9 and removable shielding sheet 44. In use, the thin film 45 of the topical brachytherapy laminate structure, which is between about 25 to 200 microns thick, is the first layer that contacts the wound surface. The thin film 45 further contains gemcitabine or other radio-sensitizer to make the tumor cells susceptible to radiation.

When water and heat is absorbed from the operative bed or wound bed, layers of the laminate structure become very flexible and stick to the irregular surface and deliver the predetermined radiation dose.

From the wound bed and heading outwards, the laminate structure comprises: a removable shielding sheet 44, for example lead vinyl and/or acrylic that is present only for handling and delivery, removed on application. The removable shielding sheet 44 may be attached peripherally to outer layer 37 with water and/or heat soluble glue for peeling away. The laminate structure further comprises a thin film of quick absorbing hydrocolloid 45 (cellulose) which is the first layer that actually touches the wound surface. This contains gemcitabine or other radio-sensitizer to make the tumor cells susceptible to radiation—can be between about 25 to 200 microns thick. The laminate structure further comprises radioisotope particles impregnated in the surface interface between layer 44 and layer 39 forming a flat sheet or thin mesh layer 45.

The hydrogel layer 37, which absorbs radiation to protect the surgeon and any other tissues while they finish the case and the radioisotope decays, may have a thickness of between about 4 to 5 mm thick to effectively absorb the particles.

Benefits of the system include that: it provides an alternative treatment to manage close or positive margins to chemotherapy with or without adjuvant radiotherapy to the operative bed; it avoids the exposure to high toxicity of conventional treatments; and the doses of radiation can be localized to the tissue margins more readily hence decrease the effect of the presence of radiosensitive surrounding structures like the bowel, no need to wait for reconstructed structures (like anastomoses) to heal before the commencement of treatment with the topical device.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A flexible brachytherapy device for application on a wound site in a body, the device comprising:

a bioresorbable carrier matrix structure comprising a plurality of radio-isotope particles, the bioresorbable carrier matrix structure configured to degrade, when implanted at the wound site, at a rate such that the bioresorbable carrier matrix structure has a half-life that is longer than a half-life of the plurality of radio-isotope particles such that activity from the plurality of radio-isotope particles is localized to the wound site, wherein the bioresorbable carrier matrix structure has a first surface and a second surface, wherein the first surface is opposite to the second surface;

a hydrophilic substrate located adjacent to the first surface of the bioresorbable carrier matrix structure, wherein the hydrophilic substrate is configured to adhere to the wound site to prevent migration of the device during the half-life of the plurality of radio-isotope particles, the hydrophilic substrate configured to degrade, when implanted at the wound site, at a rate faster than the bioresorbable carrier matrix structure; and a hydrogel substrate located adjacent to the second surface of the bioresorbable carrier matrix structure, the hydrogel substrate configured to shield radioactivity and to degrade at a rate such that the hydrogel substrate has a half-life that is longer than the half-life of the plurality of radio-isotope particles, wherein the plurality of radio-isotope particles are elements in compound molecules of calcium phosphate.

2. The device of claim 1, wherein the bioresorbable carrier matrix structure is configured with material(s) degradable by enzymatic processes.

3. The device of claim 1, wherein the bioresorbable carrier matrix structure is configured with material(s) degradable by pyrophosphatase.

4. The device of claim 1, wherein the compound molecules of calcium phosphate comprise one or more of: calcium pyrophosphate, monocalcium phosphate, dicalcium phosphate, octacalcium phosphate, tricalcium phosphate, hydroxyapatite, fluoroapatite, tetracalcium phosphate.

5. The device of claim 1, wherein the bioresorbable carrier matrix structure is amorphous or semicrystalline in nature.

6. The device of claim 5, wherein the bioresorbable carrier matrix structure is partially semicrystalline, such that the rate of degradation of the bioresorbable carrier matrix structure is based on the half-life of the plurality of radio-isotope particles and through modification of crystallinity.

7. The device of claim 1, wherein the hydrogel substrate is crosslinked with citric acid, wherein a percentage of citric acid relative to the hydrogel substrate is selected for crosslinking with the hydrogel substrate to specify the rate that the hydrogel substrate degrades to maintain structural integrity and shielding capacity.

8. The device of claim 7, wherein the percentage is between 2.5% and 10%.

9. The device of claim 7, wherein the citric acid crosslinking is catalysed by titanium oxide.

10. The device of claim 1, wherein the hydrophilic substrate comprises a coating or suspension of a haemostatic agent.

11. The device of claim 1, wherein the hydrogel substrate is combined with the bioresorbable carrier matrix structure by at least one of: mechanical integration, chemical crosslinking, or enzymatic crosslinking.

12. A method of manufacturing a flexible brachytherapy device for application on a wound site in a body, the method comprising:

forming a bioresorbable carrier matrix structure comprising a plurality of radio-isotope particles, wherein the bioresorbable carrier matrix structure is configured to degrade at a rate such that the bioresorbable carrier matrix structure has a half-life that is longer than a half-life of the radio-isotope particles such that activity from the plurality of radio-isotope particles is localized to the wound site, wherein the bioresorbable carrier matrix structure has a first surface and a second surface, wherein the first surface is opposite to the second surface;

forming a hydrophilic substrate adjacent to the first surface of the bioresorbable carrier matrix structure, wherein the hydrophilic substrate is configured to adhere to the wound site to prevent migration of the device during the half-life of the plurality of radio-isotope particles, the hydrophilic substrate configured to degrade, when implanted at the wound site, at a rate faster than the bioresorbable carrier matrix structure; and forming a hydrogel substrate adjacent to the second surface of the bioresorbable carrier matrix structure, the hydrogel substrate configured to shield radioactivity and to degrade at a rate such that the hydrogel substrate has a half-life that is longer than the half-life of the plurality of radio-isotope particles, wherein the radio-isotope particles are elements in compound molecules of calcium phosphate.

13. The method of claim 12, wherein the bioresorbable carrier matrix structure is formed by:

adsorbing or dispersing an aqueous solution of a radio-isotope to a hydrophobic [sub stance] *substance*.

14. The method of claim 13, wherein the hydrophobic substance comprises a hydrophilic surface.

15. The method of claim 13, wherein the aqueous solution comprises radioactive ions.

16. The method of claim 12, wherein the bioresorbable carrier matrix structure is formed by:

precipitating the radio-isotope to form a plurality of insoluble radio-isotope particles in the bioresorbable carrier matrix structure.

17. The method of claim 16, wherein precipitating the radio-isotope is performed with a precipitant comprising an aqueous solution of calcium ions.

18. The method of claim 17, wherein the precipitant comprises one or more of calcium chloride calcium hydroxide, calcium nitrate, or calcium bromide.

19. The method of claim 12, wherein the bioresorbable carrier matrix structure is formed by:

adsorbing or dispersing an aqueous solution of a radio-isotope to an amorphous or semicrystalline hydrophobic substance to provide the bioresorbable carrier matrix structure.

20. The method of claim 12, wherein the compound molecules of calcium phosphate comprise one or more of: calcium pyrophosphate, monocalcium phosphate, dicalcium phosphate, octacalcium phosphate, tricalcium phosphate, hydroxyapatite, fluoroapatite, tetracalcium phosphate.

21. The method of claim 12, wherein the hydrophilic substrate comprises a coating or suspension of a haemostatic agent.

*22. A multi-layered bioresorbable brachytherapy device, comprising:*

*a sealed source of radiotherapy formed by hydrophobic or partially hydrophobic layers, wherein the hydrophobic or partially hydrophobic layers form a receptacle, and*

*a plurality of radio-isotope particles received within the receptacle,*

*wherein the receptacle is disposed between a radioactive shielding layer and a hydrophilic substrate to form the multi-layered bioresorbable brachytherapy device, the radioactive shielding layer comprising a hydrogel layer,*

*wherein the hydrophobic or partially hydrophobic layers are configured to degrade, when implanted at a wound site, at a rate whereby the sealed source of radiotherapy persists for at least one half-life of the plurality of radio-isotope particles, such that activity from the plurality of radio-isotope particles is localized to the sealed source for at least one half-life of the plurality of radio-isotope particles,*

*wherein the hydrogel substrate is configured to degrade, when implanted at a wound site, at a rate whereby the hydrogel substrate shields radioactivity for at least one half-life of the plurality of radio-isotope particles.*

*23. The device of claim 22, wherein the plurality of radio-isotope particles comprise a beta emitter.*

*24. The device of claim 22, wherein the plurality of radio-isotope particles comprises one or more of: Yttrium-90, Iridium-192, Palladium-103, Caesium-131, Iodine-131, Iodine-125, Iodine-123, 33-phosphorus, 32-phosphorus, or a ratio of 33-phosphorus to 32-phosphorus, and/or compounds containing such isotopes.*

*25. The device of claim 22, wherein the plurality of radio-isotope particles comprise an insoluble or poorly soluble salt capable of being bio-resorbed in a body.*

*26. The device of claim 22, wherein the sealed source of radiotherapy is obtained through lamination of the radio-isotope particles with the hydrophobic or partially hydrophobic layers.*

*27. The device of claim 22, wherein the hydrophilic substrate is configured to adhere to a wound site to prevent migration of the device for at least one half-life of the plurality of radio-isotope particles.*

*28. The device of claim 22, wherein the hydrogel substrate is crosslinked with citric acid, wherein a percentage of citric acid relative to the hydrogel substrate is selected for cross-linking with the hydrogel substrate to specify the rate that the hydrogel substrate degrades to maintain structural integrity and shielding capacity.*

*29. The device of claim 28, wherein the percentage is between 2.5% and 10%.*

*30. The device of claim 28, wherein the citric acid crosslinking is catalyzed by titanium oxide.*

*31. The device of claim 22, wherein the hydrophilic substrate comprises a coating or suspension of a haemostatic agent.*

*32. A method of treatment to manage close or positive margins of a wound site in a body including using the device of claim 22 and applying the device to the wound site in the body with the hydrophilic substrate facing the wound site and the hydrogel layer being arranged to protect a surgeon and other tissues of the body.*

*33. A method for minimizing and/or controlling local recurrence of malignant cancer and seroma on a wound site in a body following cancer surgery, the method comprising using the device of claim 22 and applying the device to the wound site in the body with the hydrophilic substrate facing the wound site and the hydrogel layer being arranged to protect a surgeon and other tissues of the body.*

*34. A method for minimizing and/or controlling uncontrolled growth of microscopic tumor cells at margins of a wound site in a body including using the device of claim 22 and applying the device to the wound site in the body with the hydrophilic substrate facing the wound site and the hydrogel layer being arranged to protect a surgeon and other tissues of the body.*

* * * * *